(12) United States Patent
Okada

(10) Patent No.: US 7,935,106 B2
(45) Date of Patent: May 3, 2011

(54) TREATMENT TOOL FOR ENDOSCOPE

(75) Inventor: Tsutomu Okada, Tokyo (JP)

(73) Assignee: Olympus Corporation, Tokyo (JP)

( * ) Notice: Subject to any disclaimer, the term of this patent is extended or adjusted under 35 U.S.C. 154(b) by 174 days.

(21) Appl. No.: 11/366,689

(22) Filed: Mar. 2, 2006

(65) Prior Publication Data

US 2006/0149222 A1 Jul. 6, 2006

(30) Foreign Application Priority Data

Sep. 9, 2003 (JP) ................... P2003-316495
Feb. 24, 2004 (JP) ................... P2004-047515

(51) Int. Cl.
*A61B 17/00* (2006.01)
*A61B 1/00* (2006.01)
(52) U.S. Cl. ................. 606/1; 600/104; 606/205
(58) Field of Classification Search .......... 600/104, 600/106, 118, 105, 135, 108; 606/1, 205–209, 606/113
See application file for complete search history.

(56) References Cited

U.S. PATENT DOCUMENTS

| | | | | |
|---|---|---|---|---|
| 3,404,677 A | * | 10/1968 | Springer | 600/564 |
| 4,158,746 A | * | 6/1979 | Taylor et al. | 174/112 |
| 4,345,599 A | * | 8/1982 | McCarrell | 606/113 |
| 4,632,110 A | * | 12/1986 | Sanagi | 606/207 |
| 4,815,476 A | * | 3/1989 | Clossick | 600/564 |
| 5,238,002 A | * | 8/1993 | Devlin et al. | 600/564 |
| 5,275,614 A | * | 1/1994 | Haber et al. | 606/207 |
| 5,762,613 A | * | 6/1998 | Sutton et al. | 600/564 |
| 6,162,207 A | * | 12/2000 | Ouchi | 606/1 |
| 6,258,101 B1 | * | 7/2001 | Blake, III | 606/113 |

FOREIGN PATENT DOCUMENTS

| | | |
|---|---|---|
| JP | H02-224651 | 9/1990 |
| JP | H03-53211 | 5/1991 |
| JP | 6-197900 | 7/1994 |
| JP | H08-131451 | 5/1996 |
| JP | 2001-275947 | 10/2001 |
| JP | 2002-17665 | 1/2002 |
| JP | 2002-263110 | 9/2002 |
| JP | 3370601 | 11/2002 |
| JP | 2003-111765 | 4/2003 |

OTHER PUBLICATIONS

Japanese Office Action dated Jan. 26, 2010 with translation.

* cited by examiner

*Primary Examiner* — Linda C Dvorak
*Assistant Examiner* — Alireza Nia
(74) *Attorney, Agent, or Firm* — Scully, Scott, Murphy & Presser, P.C.

(57) ABSTRACT

In a forceps 1 of the present invention, an operating section 12 is provided with a main body 12 and a pair of slider sections 13 which advance and retract an operating wire 11 by relative closing-and-departing motions thereof; the slider section 13 is provided with a thumb hole section 16 to which a thumb is engaged to operate the operating section 12; the main body 12 is provided with a second finger-receiving section 21 having a sandwiched section 21a to be sandwiched between a first finger and a second finger and thereby being engaged with the first finger and the second finger; and when an operating duct section 6 is inserted within a forceps channel, a distance from the second finger-receiving section 21 to a forceps opening is longer than a distance from a thumb hole section 16 to the forceps opening.

28 Claims, 21 Drawing Sheets

TREATMENT TOOL FOR ENDOSCOPE

This application is a Continuation application of International Patent Application No. PCT/JP2004/013293, filed on Sep. 7, 2004, which claims priority from Japanese Patent Application No. 2003-316495, filed Sep. 9, 2003, and Japanese Patent Application No. 2004-047515, filed Feb. 24, 2004, the contents of which are incorporated herein.

TECHNICAL FIELD

The present invention relates to a treatment tool for an endoscope which is used by inserting it into a forceps channel of the endoscope.

BACKGROUND ART

A treatment tool for a hard endoscope is provided, on a bottom end thereof, with a slider which performs advancing and retracting operations of a distal operation section provided on a distal end side thereof. This slider has hole-shaped finger-receiving sections which are formed therein so as to be engageable with fingers during operations (for example, refer to FIG. 1 of Japanese Unexamined Patent Application, First Publication No. H08-131451).

On the other hand, a treatment tool for a flexible endoscope which is used by inserting it into a forceps channel of a flexible endoscope is provided with a finger-receiving member having sections which are engageable with fingers so as to operate this flexible endoscope.

As for this kind of treatment tools for an endoscope, one is proposed which is maintained in a manner such that an operation section stands on a forceps opening and does not descend; thereby, enabling stable operations by an operator of the endoscope (for example, refer to FIG. 1 of Japanese Utility Model, Publication No. H03-53211).

In the case in which the above-mentioned conventional treatment tool for an endoscope is operated by making it stand on the forceps opening, the finger-receiving section for a thumb is disposed on the upside, while the finger-receiving sections for a first finger and a second finger are disposed on the lower side. Therefore, finger arrangement will be opposite to an arrangement which is comfortable for a hand while holding an operation section. That is, as shown in the conventional treatment tool for an endoscope of FIG. 25, the operation section has to be gripped while bending the wrist during the operations.

In addition, there has been a conventional tool for an endoscope having a treatment tool distal end section which is operated by operating an operation section provided on the bottom end side, wherein: the operation section is provided on the bottom side of a sheath so as to be coaxial with the sheath; furthermore, a first finger engaging portion is provided on the bottom side of the operation section; and furthermore, a second finger engaging portion to which an operation wire is connected, is attached to a shaft body provided on the bottom side of the sheath so as to be advanceable and retractable (for example, refer to the Patent Publication No. 3,370,601). With this treatment tool for an endoscope, the operating section is held by engaging a thumb onto the first finger engaging portion and engaging other fingers onto the second finger engaging portion.

Furthermore, as for another example of the conventional operating section, there is one which is held by: engaging a thumb onto a ring connected to an operating wire; and sandwiching a grip provided on the bottom end side of a flexible operation duct section with the other fingers (for example, refer to FIG. 1 of Japanese Unexamined Patent Application, First Publication No. H02-224651).

When an operator of the endoscope operates the treatment tool for an endoscope using the above-mentioned operating section, as shown in the conventional treatment tool for an endoscope of FIG. 26, an operating section 119B will be held by turning the direction of a sheath 102B protruding from a forceps opening 123B of an endoscope 122B.

DISCLOSURE OF INVENTION

The present invention adopts the following.

A treatment tool for an endoscope of the present invention includes: an operating duct section which is to be inserted into a forceps channel of the endoscope; a treatment tool distal section which is provided on a distal end side of this operating duct section; and an operating section which is provided on a bottom end side of the operating duct section, wherein: the operating duct section includes an operating wire of which one end is joined to the treatment tool distal end; and the operating section includes a pair of driving-operation sections which advance and retract the operating wire by relative closing-and-departing motions thereof; and wherein: one of the pair of driving-operation sections is provided with a first finger-receiving section to which a finger which operates the operating section is engaged, while the other is provided with a second finger-receiving section which has a sandwiched section to be sandwiched between the other fingers, and onto which the other fingers are to be engaged; and an arrangement thereof is made such that, when the operating duct section is inserted within the forceps channel, a distance from the second finger-receiving section to an opening of the forceps channel on the operating section side of the endoscope becomes longer than a distance from the first finger-receiving section to the opening of the forceps channel, on the operating section side of the endoscope.

It is preferable that the first finger-receiving section is a one hole-section to which a thumb which operates the operating section is engaged.

It may be arranged such that: the operating duct section is flexible; and the operating section includes a hard joint-section which connects this operating section onto a forceps opening of the forceps channel so as to make it stand thereon.

It may be arranged such that one of the pair of driving-operation sections, on a movable side, and another end of the operating wire are joined via a turning member having hardness and a substantial U-shape.

It may be arranged such that a bottom end of the operating wire is joined to the first finger-receiving section.

It may be arranged such that a bottom end of the operating wire is joined to the second finger-receiving section.

A treatment tool for an endoscope of the present invention includes: an operating duct section which is to be inserted into a forceps channel through a forceps opening of the endoscope; a treatment tool distal section which is joined to a distal end side of this operating duct section; and an operating section which is joined to a bottom end side of the operating duct section and operates the treatment tool distal section, wherein: the operating duct section includes an operating wire which drives the treatment tool distal section; the operating section includes: a body of which one end is joined to a bottom end of the operating duct section, and stands on the forceps opening while the operating duct section is inserted within the forceps channel; and a slider section which is joined to a bottom end of the operating wire, and is advanceable and retractable between one end and the other end of the body; and the slider section is provided with one first finger-receiving section, while the other end of the body is provided with a second finger-receiving section.

It is preferable that the first finger-receiving section has a shape that is engageable with a thumb, while the second finger-receiving section has a shape that is engageable with the other fingers.

It may be arranged such that: the first finger-receiving section is a thumb hole section through which a thumb is inserted; the second finger-receiving section is one or a plurality of hole sections through which other fingers are inserted; and a linear line connecting between a center of the hole sections and a center of the thumb hole section is parallel to an advancing-and-retracting direction of the slider section.

It may be arranged such that a distal end of the main body is provided with a hard joint-member which is connected to the forceps channel.

It may be arranged such that the operating section is provided with an attaching portion which is attached to and is detached from the forceps opening.

A treatment tool for an endoscope of the present invention includes: a flexible operating duct section which is to be inserted into a forceps channel through a forceps opening of an endoscope; a treatment tool distal section which is joined to a distal end side of this operating duct section; and an operating section which is joined to a bottom end side of the operating duct section and operates the treatment tool distal section, wherein:

the operating duct section includes an operating wire which drives the treatment tool distal section; and the operating section includes: a first driving-operation section which is supported beside the operating duct section; a second driving-operation section which is provided on a side of the treatment tool distal end section than the first driving-operation section, and advances and retracts with respect to the first driving-operation section; and a turning member which joins between the second driving-operation section and a bottom end of the operating wire, and has hardness and a substantial U-shape.

It may be arranged such that: the second driving-operation section includes an extending portion which extends towards a rear end side of this treatment tool for an endoscope by way of the first driving-operation section; and the turning member is joined to this extending portion.

It may be arranged such that the second driving-operation section has a shape that is engageable with a thumb, while the first driving-operation section has a shape that is engageable with the other fingers.

Furthermore, it may be arranged such that: a third driving-operation section which forms one unit together with the first driving-operation section is provided on a rear side of the first driving-operation section; a fourth driving-operation section is provided on a rear end of the extending portion; and this fourth driving-operation section is disposed between the first driving-operation section and the third driving-operation section.

It may be arranged such that the third driving-operation section has a shape that is engageable with a thumb, while the fourth driving-operation section has a shape that is engageable with the other fingers.

It may be arranged such that the first driving-operation section is fixed in a manner such that rotation thereof is restricted with respect to the operating duct section.

It may be arranged such that the first driving-operation section is provided so as to be rotatable with respect to the operating duct section around an axis of this operating duct section.

It may be arranged such that: the first driving-operation section and the second driving-operation section have shapes which are similar to each other; the third driving-operation section and the fourth driving-operation section have shapes which are similar to each other; and the first driving-operation section and the third driving-operation section have shapes which are different from each other.

It may be arranged such that: the first driving-operation section and the second driving-operation section have colors which are the same as each other; the third driving-operation section and the fourth driving-operation section have colors which are the same as each other; and the color of the first driving-operation section is different from the color of the third driving-operation section.

It may be provided with a distinguishing means which, at least, combines the first driving-operation section and the second driving-operation section, combines the third driving-operation section and the fourth driving-operation section, and distinguishes the first driving-operation section and the third driving-operation section.

BEST MODE FOR CARRYING OUT THE INVENTION

First Embodiment

Figure 1:
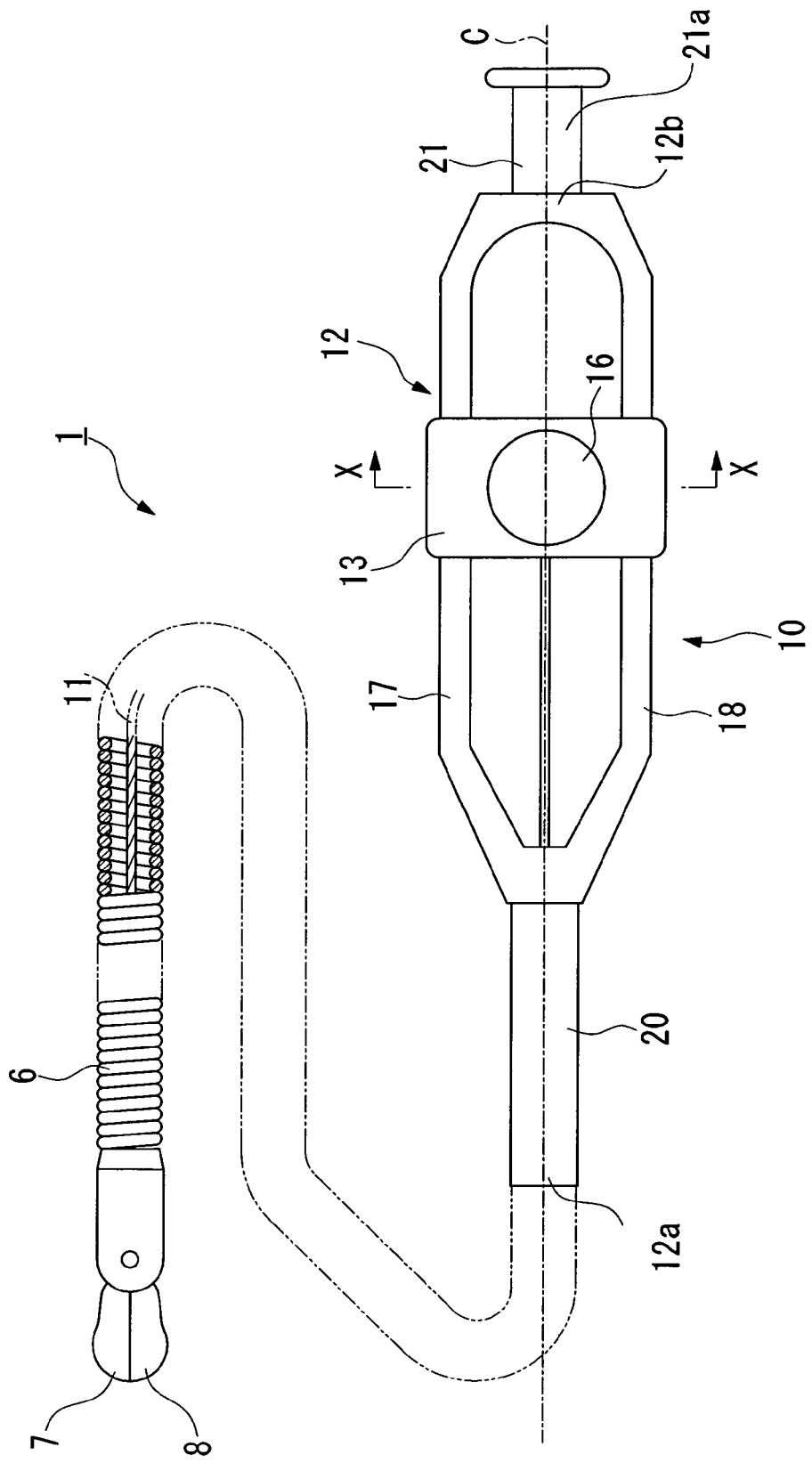
FIG. 1 is a side view of a treatment tool for an endoscope according to a first embodiment of the present invention, wherein one portion thereof is shown as a cross-sectional view.
Figure 2:
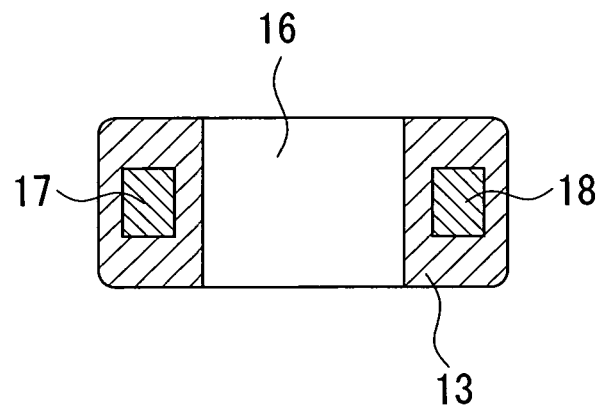
FIG. 2 is an X-X cross-sectional view of FIG. 1.

A first embodiment of a treatment tool for an endoscope of the present invention will be explained hereinafter with reference to FIG. 1 to FIG. 4.

A forceps (the treatment tool for an endoscope) 1 of the present embodiment is provided with: a flexible operating duct section 6 which is to be inserted into a forceps channel 5 through a forceps opening 3 of an endoscope 2; a pair of clamp pieces (a treatment tool distal end section) 7 and 8 which are connected to the distal end side of the operating duct section 6; and an operating section 10 which is connected to the bottom end side of the operating duct section (a sheath) 6 and operates opening and closing of the pair of clamp pieces 7 and 8.

An operating wire 11 for opening and closing the pair of clamp pieces 7 and 8 by advancing-and-retracting operations of the operating section 10, is provided inside the operating duct section 6.

The operating section 10 is provided with: a main body 12 which is provided so as to stand on the forceps opening 3 when one end 12a is fixed to a bottom end side of the operating duct section 6 and the operating duct section 6 is inserted inside the forceps channel 5; and a slider section 13 which is connected to a bottom end of the operating wire 11 and is advanceable and retractable between one end 12a and another end 12b of the main body 12.

The slider section 13 has a substantially plate-shape. Furthermore, this slider section 13 has a thumb hole section (a first finger-receiving section) 16 through which a thumb is insertable; and the thumb hole section 16 is formed at a position where is on a center axis C of the main body 12, and is also on an extension axis line of the operating wire 11. The size of the thumb hole section 16 preferably has an internal diameter of, for example, about 30 mm.

A center portion of the main body 12 is bored from the one end side 12a to the another end side 12b. In addition, both end portions of the main body 12 in the width direction form two parallel rails 17 and 18 extending parallel with respect to the operating wire 11, while sandwiching the operating wire 11 at the center therebetween.

Figure 3A:
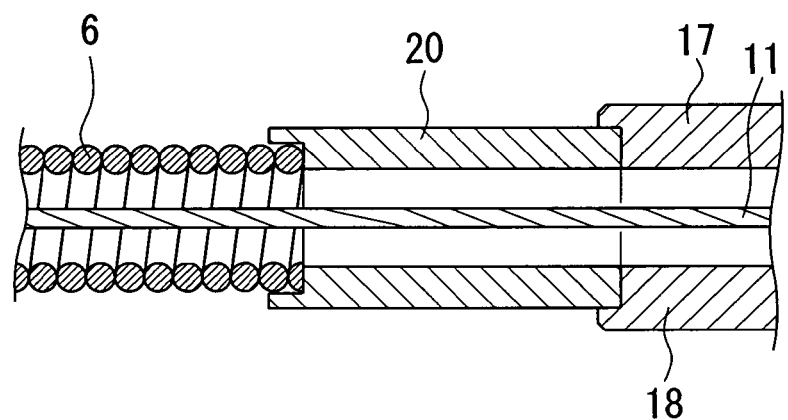
FIGS. 3A and 3B are cross-sectional views showing a hard joint-member of the same treatment tool for an endoscope.
Figure 4:
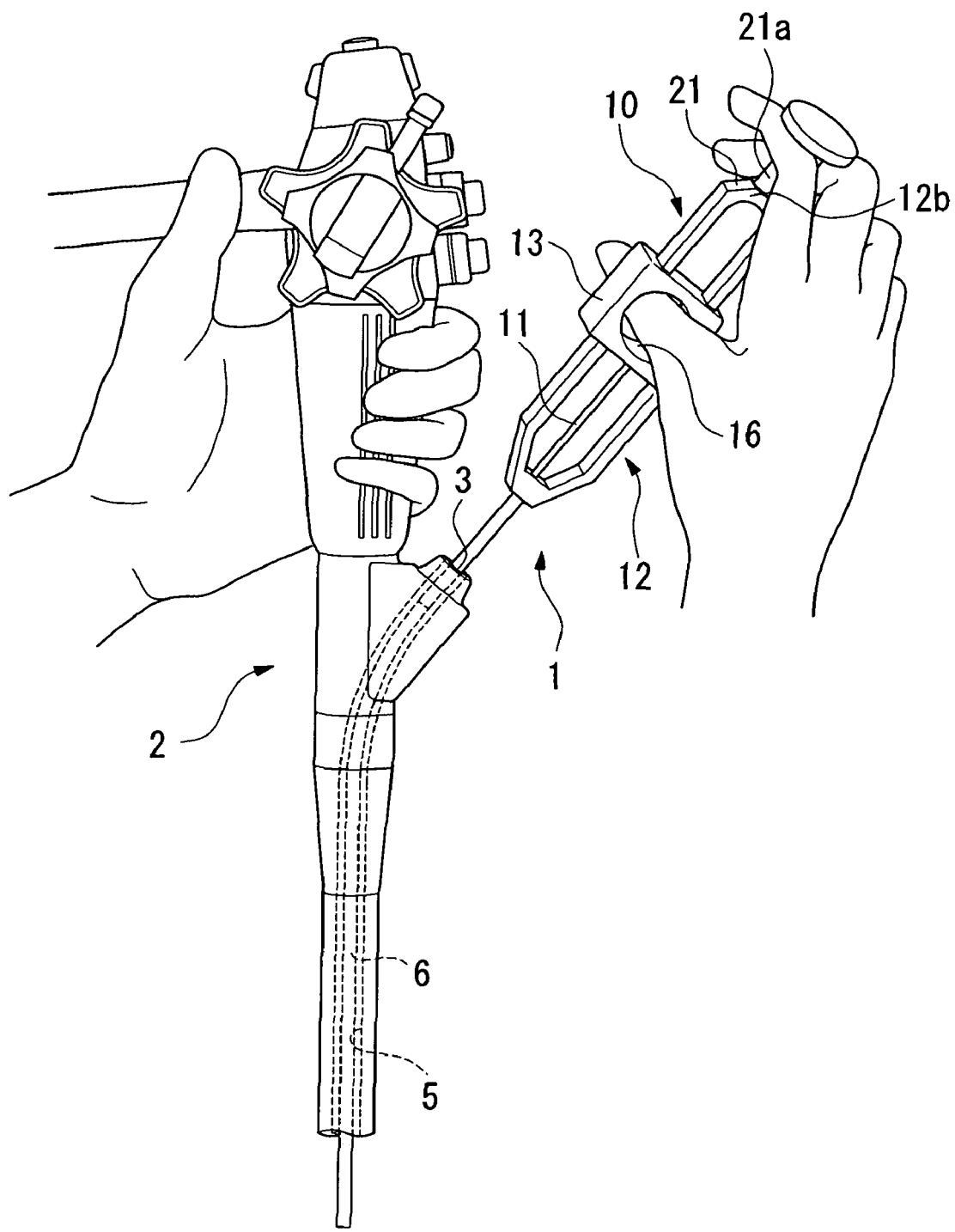
FIG. 4 is a drawing explaining how to use the same treatment tool for an endoscope.

The one end 12a being a distal end of the main body 12 is provided with a hard joint-member 20 which is connectable with respect to the forceps channel 5. As shown in FIG. 3A, a bottom end of the operating duct section 6 is connected to a distal end of the hard joint-member 20. In addition, as shown in FIG. 1 and FIG. 4, the another end 12b is provided, on the center axis C of the main body 12, with a cylinder-shaped second finger-receiving section 21 having a sandwiched section 21a to be sandwiched between other fingers such as a first finger and a second finger and the like, and to which the other fingers are engageable. Furthermore, when the operating duct section 6 is inserted within the forceps channel 5, the second finger-receiving section 21 is disposed at a higher position in the vertical direction than the thumb hole section 16.

The slider section 13 is attached to the rails 17 and 18 so as to cross over the two rails 17 and 18. In addition, this slider section 13 performs advancing-and-retracting operations so as to slide along the rails 17 and 18.

Figure 3B:
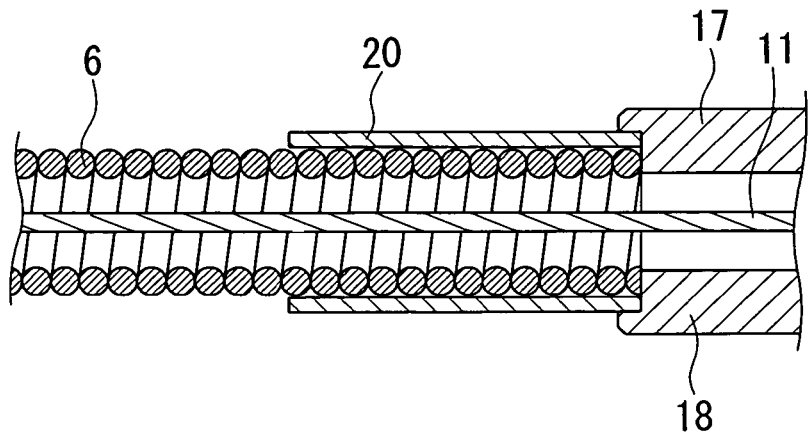

Moreover, as shown in FIG. 3B, the operating duct section 6 may be connected so as to penetrate the inside of the hard joint-member 20.

Next, how to operate the forceps 1 according to the present embodiment will be explained.

Firstly, the forceps 1 is inserted into the forceps opening 3, from the side of the pair of clamp pieces 7 and 8. Furthermore, the operating duct section 6 is inserted into the forceps channel 5, and the hard joint-member 20 is connected into the forceps channel 5. By this, the operating duct section 10 is attached so as to stand on the forceps opening 3 without descending from the forceps opening 3.

When operating the forceps 1, an operator engages his or her thumb with the thumb hole section 16 and also engages his or her first finger and second finger with the second finger-receiving section 21 so as to sandwich the sandwiched section 21a therebetween, while raising his or her hand upright.

Like this, opening and closing operations of the pair of clamp pieces 7 and 8 can be performed by performing sliding operations of the slider section 13 within a range between the thumb which is disposed on the one end side 12a of the main body 12, and the first finger and the second finger which are disposed on the another end side 12b of the main body.

According to the above-explained forceps 1 of the present embodiment, when the operating section 10 is operated while it is provided so as to stand on the forceps opening 3, the thumb will be disposed on the lower side within the operating section 10 while the first finger and the second finger will be disposed on the upper side within the operating section 10. Accordingly, it becomes possible to reliably perform sliding operations of the slider section 13 while simply maintaining easy posture of a hand of an operator, without twisting a wrist like when using the conventional treatment tool for an endoscope.

In addition, since the operating direction of the finger is made so as to follow the sliding direction of the slider section 13, operations of the slider section 13 become easy; thereby, enabling operations without applying wasteful power during the operations of the slider section 13.

Furthermore, since connection to the forceps channel 5 is made by inserting the hard joint-section 20 into the forceps opening 3, the operating section 10 can be held in a stable standing-state by the hardness of the hard joint-section 20; thereby, enabling stable operations of the operating section 10 to be maintained.

Second Embodiment

Figure 5:
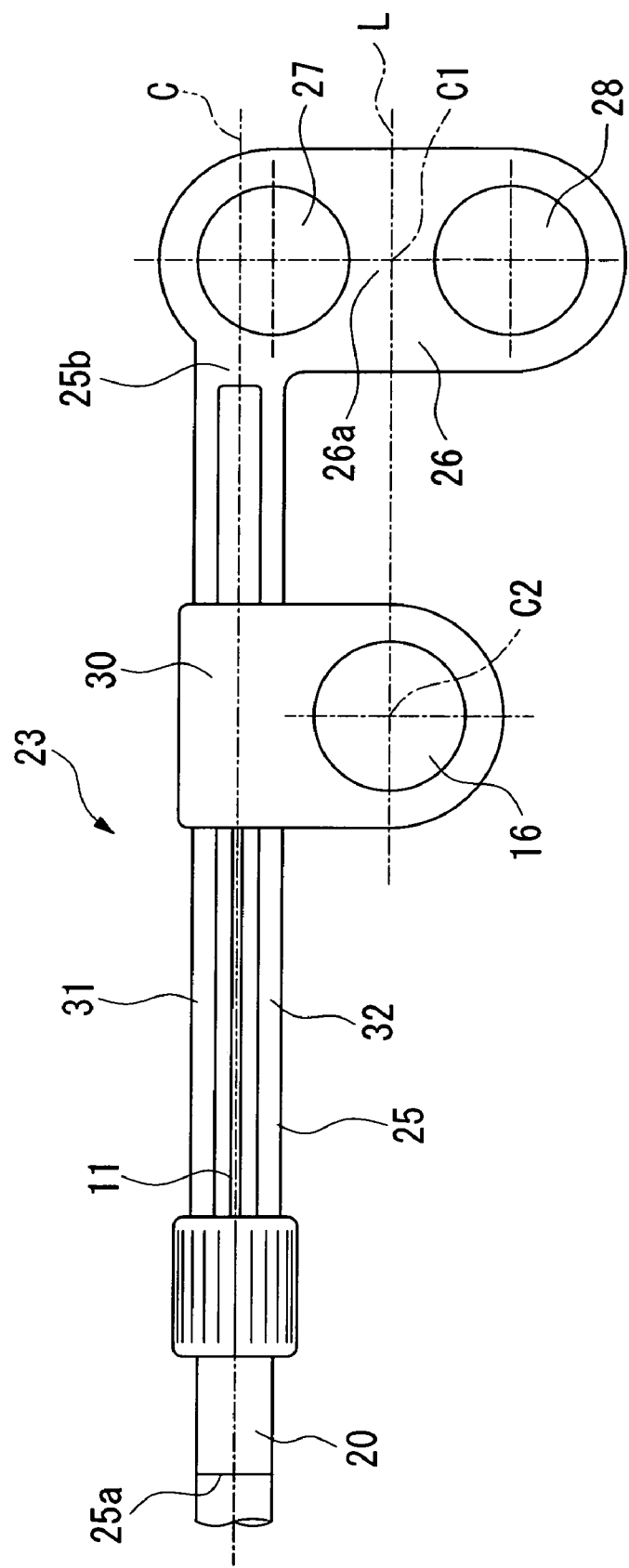
FIG. 5 is a side view of an operating section of a treatment tool for an endoscope according to a second embodiment of the present invention.
Figure 6:
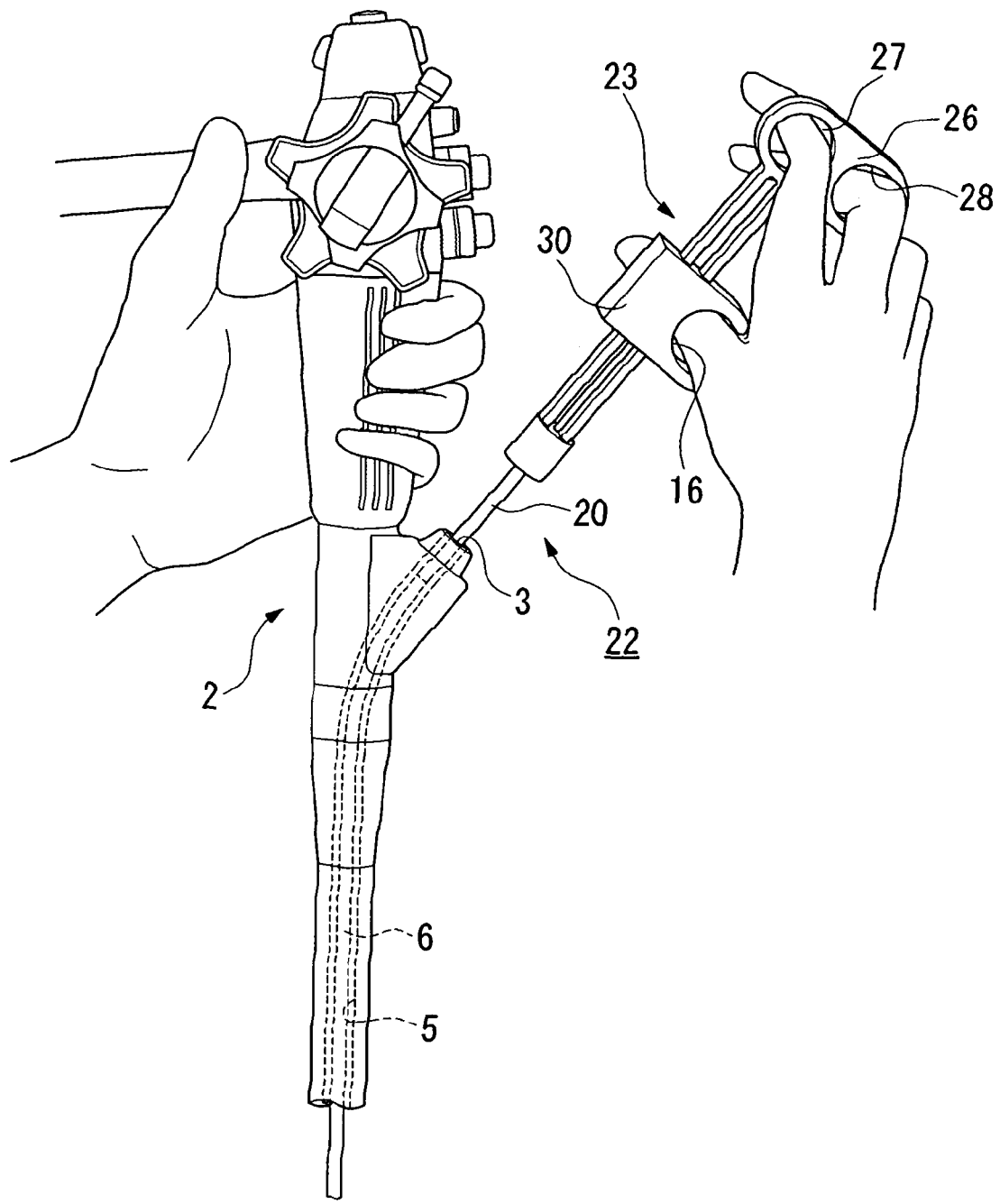
FIG. 6 is a drawing explaining how to use the same treatment tool for an endoscope.

Next, a second embodiment of a treatment tool for an endoscope of the present invention will be explained with reference to FIG. 5 and FIG. 6. Moreover, through the explanation of the present embodiment, the same reference symbols will be applied to the same configuration elements as the ones explained in the above-mentioned first embodiment, and the explanations thereof will be omitted here.

The different point of the present embodiment with respect to the above-mentioned first embodiment is that: in a forceps 22 of the present embodiment, a second finger-receiving section 26 of a main body 25 of an operating section 23 is provided with a hole section for a first finger (a hole section) 27 through which the first finger is insertable and a hole section for a second finger (a hole section) 28 through which a second finger is insertable; and a line connecting a center C1 between the hole section for a first finger 27 and a hole section for a second finger 28, and a center C2 of the thumb hole section 16 is disposed in parallel with respect to the center axis C of the main body 25 so as to depart from the center axis C in order to avoid interferences between the main body 25 and the thumb hole section 26, although, in the above-mentioned first embodiment, the thumb hole section 16 and the second finger-receiving section 21 are disposed on the center axis C of the main body 12 of the operating section 10. In addition, the thumb hole section 16, the hole section for a first finger 27, and the hole section for a second finger 28, of the present embodiment are arranged on the same flat plane, and center axes of each hole are made perpendicular to a plane which includes the center axis C and a linear line L.

The main body 25 has a substantial rod-shape, and a center portion thereof is removed from one end side 25a to another end side 25b. In addition, a first rail 31 and a second rail 32 each extending in parallel with respect to the center axis C are formed at both end sections in the width direction of the main body 25.

A slider section 30 is formed in a plate-shape which extends, along the width direction of the main body 25, from a position of the first rail 31 to a position departing from a position of the second rail 32 by way of the position of the second rail 32. In addition, this slider section 30 is engaged with each of the first rail 31 and the second rail 32, and is operated so as to advance and retract along these first rail 31 and second rail 32.

The slider section 30 is formed with a thumb hole section (a first finger-receiving section) 16 at a position departing from the second rail 32.

A hard joint-member 20 which is connectable with respect to the forceps channel 5 is provided at the one end 25a of the main body 25. In addition, at the another end 25b of the main body 25, a second finger-receiving section 26 having a substantial plate-shape extends from the second rail 32 towards the width direction of the main body 25.

The hole section for a first finger 27 and the hole section for a second finger 28 are arranged in the perpendicular direction with respect to the center axis C of the main body 25 and the linear line L. In addition, these hole section for a first finger 27 and hole section for a second finger 28 are arranged axisymmetrically with respect to the linear line L; and the hole section for the second finger 28 is disposed at a further position from the center axis C than the hole section for the first finger 27. Furthermore, a sandwiched portion 26a to be sandwiched between a first finger and a second finger when operating the operating section 23, is provided between the hole section for a first finger 27 and the hole section for a second finger 28.

Next, how to operate the forceps 22 of the present embodiment will be explained.

Firstly, the same as in the above-mentioned first embodiment, the operating section 23 of the forceps 22 is attached onto the forceps opening 3 in a manner such that the operating section 23 stands on the forceps opening 3, by connecting the hard joining-member 20 into the forceps channel 5.

When operating the forceps 22, a thumb is engaged with the thumb hole section 16, while engaging each of a first finger and a second finger with the hole section for a first finger 27 and the hole section for a second finger 28 of the second finger-receiving section 26.

Like this, opening and closing operations of the pair of clamp pieces 7 and 8 can be performed by performing sliding operations of the slider section 30 between the thumb disposed on the side of one end 25a and the first finger and the second finger disposed on the side of the another end 25b of the main body 25.

Moreover, not only the first finger and the second finger, but also a third finger and a little finger may be engaged with the hole section for a first finger 27 and the hole section for a second finger 28.

According to the above-explained forceps 22 of the present embodiment, the same operations and advantages can be obtained. Furthermore, according to the forceps 22 of the present embodiment, the hole section for a first finger 27 and the hole section for a second finger 28 are formed within the second finger-receiving section 26, and each position thereof is arranged at the above-mentioned positions; therefore, by engaging the first finger and the second finger with the hole section for a first finger 27 and the hole section for a second finger 28 for each, operations of the slider section 30 becomes easier, while enabling the operations to be performed with an easier posture since there is no necessity to apply wasteful power during the operations.

Moreover, in the present embodiment, the second finger-receiving section 26 is provided with two of the hole section for a first finger 27 and the hole section for a second finger 28; however, it is not limited to two, and one large long hole may be adopted by connecting the hole section for a first finger 27 and the hole section for a second finger 28 into one. Otherwise, equal to or more than three may be adopted.

In addition, an attaching element (not shown in the figures) for detachably fixing the operating section 23 with respect to the forceps opening 3 may be provided at a distal end of the main body 25 of the operating section 23. In this case, by attaching and fixing the above-mentioned attaching element onto the forceps opening 3, the operating section 23 can be provided so as to stand on the forceps opening 3 in the more stable manner.

Figure 7:
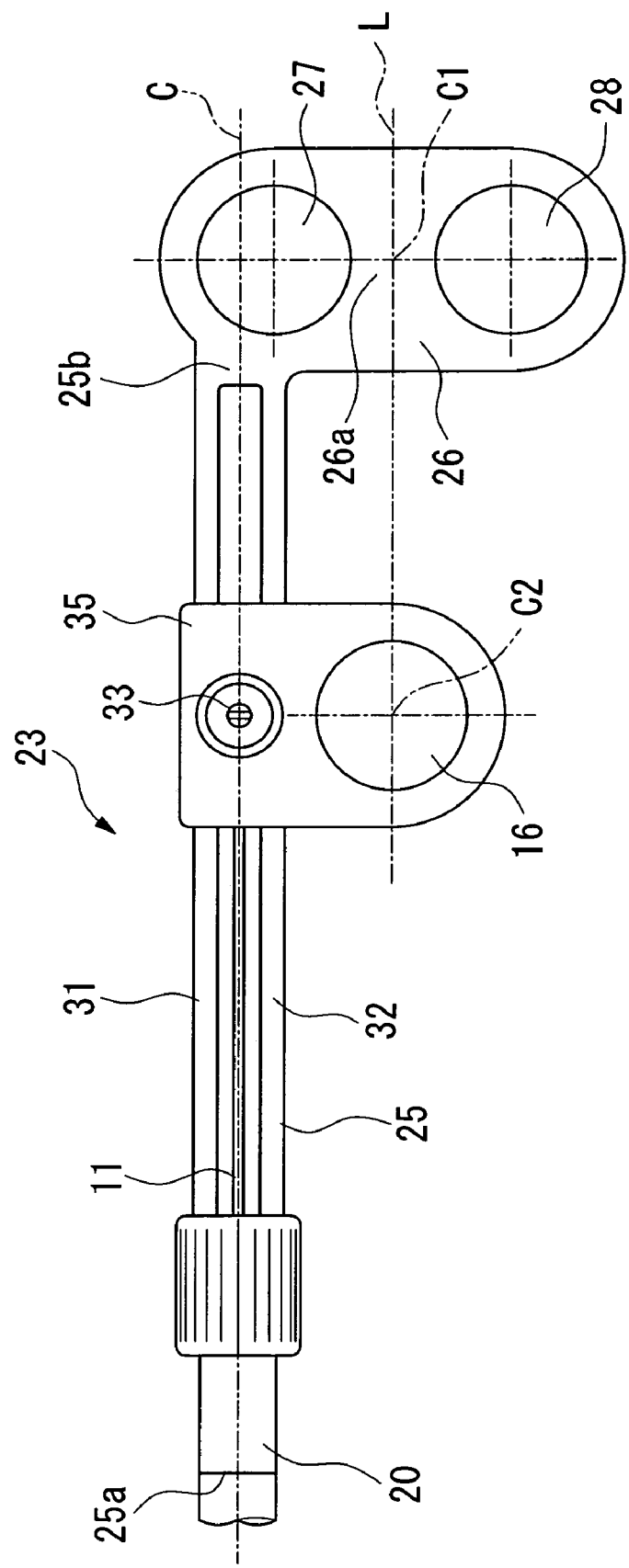
FIG. 7 is a side view of another example of an operating section of the same treatment tool for an endoscope.

Furthermore, when utilizing a high-frequency treatment tool, for a treatment tool for an endoscope, as shown for example in FIG. 7, by arranging a plug 33 for applying high-frequency current onto a slider section 35, the same operation as the one described in the above becomes possible.

Third Embodiment

Next, a third embodiment of a treatment tool for an endoscope of the present invention will be explained with reference to FIG. 8 to FIG. 13.

Figure 8:
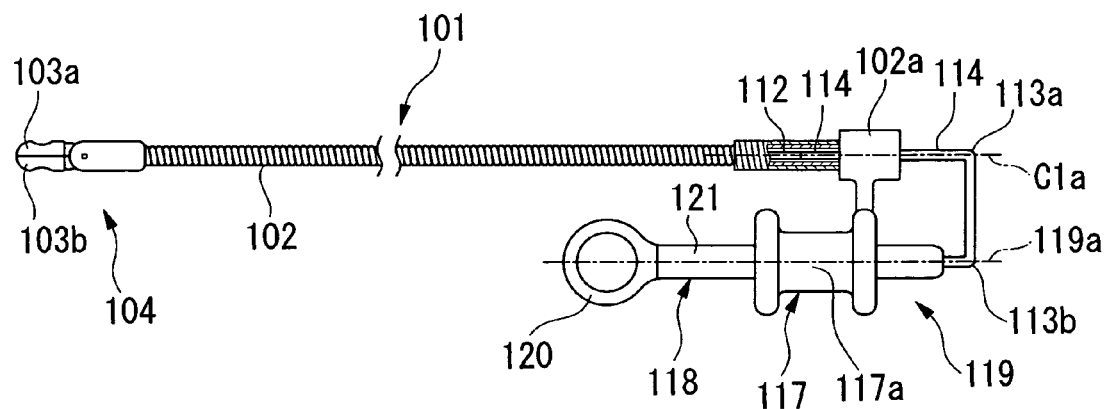
FIG. 8 is a side view showing a configuration of a treatment tool for an endoscope according to a third embodiment of the present invention.
Figure 9:
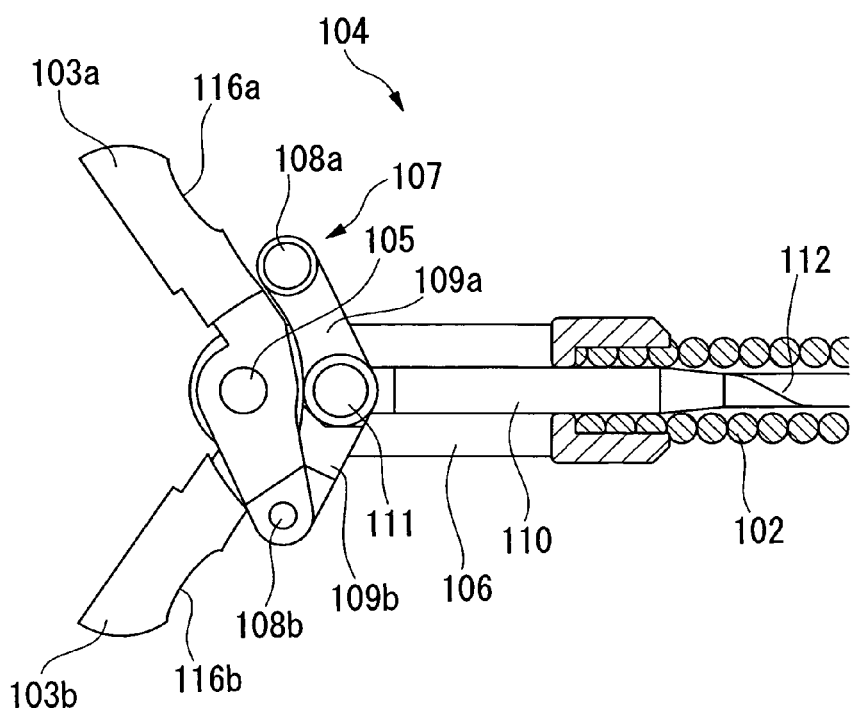
FIG. 9 is a cross-sectional view showing a configuration of a distal end portion of the same treatment tool for an endoscope, and also showing the state in which a pair of clamp cups are opened.

FIG. 8 shows a biopsy forceps (a treatment tool for an endoscope) 101 of the present embodiment. This biopsy forceps 101 is provided with a flexible sheath 102 made of a coil having a short pitch. A treatment tool distal end section 104 having a pair of biopsy cups 103a and 103b is attached onto a distal end section of the flexible sheath 102. As shown in FIG. 9, the treatment tool distal end section 104 is configured by: the pair of biopsy cups 103a and 103b; a supporting body 106 which pivotably supports the pair of biopsy cups 103a and 103b such that they freely open and close by a support axis 5; and a pantagraph mechanism 107 which is provided within this supporting body 106 and performs opening and closing operations of the biopsy cups 103a and 103b. The biopsy cup 103a and the biopsy cup 103b have the same shape.

The pantograph mechanism 107 is provided with: links 109a and 109b of which one of each end thereof is joined with each of rearward-extending arms (i.e., each portion extending toward the bottom end side) of the biopsy cups 103a and 103b by supporting pins 108a and 108b; and a supporting axis 111 for joining other ends of these links 109a and 109b to a joining member 110.

A distal end of the operating wire 112 is fixed onto a rear end of the joining member 110. This operating wire 112 is inserted within the flexible sheath 102. In addition, a rear end of the operating wire 112 is, as shown in FIG. 8, connected to a turning member 114 which is bent so as to have a substantial U-shape with bending portions 113a and 113b. An inserting section of the biopsy forceps 101 is configured by the operating wire 112 and the flexible sheath 102.

A bottom section 106a of the supporting body 106, which is joined with the flexible sheath 102, has a substantial tubular-shape. At the distal end side of the supporting body 106, two supporting sections 106b extending towards the distal end side so as to be in parallel with each other, are provided; and the biopsy cups 103a and 103b are rotatably supported by these supporting sections 106b.

Figure 10:
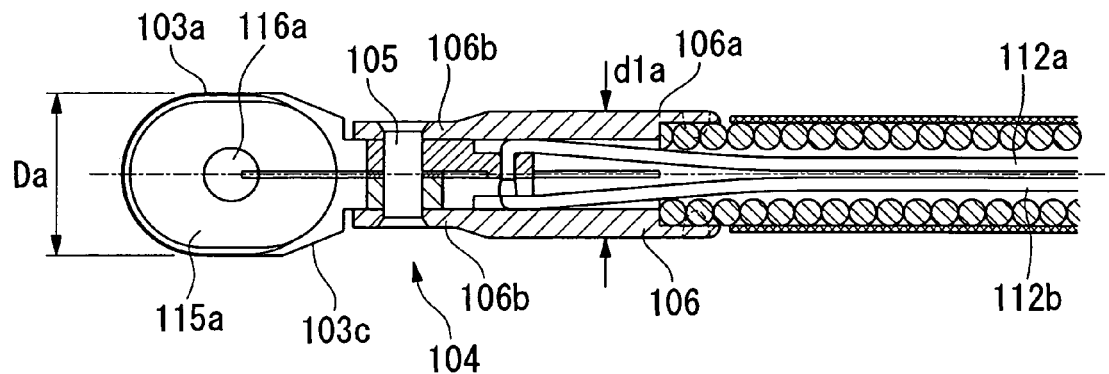
FIG. 10 is a planar cross-sectional view showing another example of a treatment tool distal end section of the same treatment tool for an endoscope.
Figure 11:
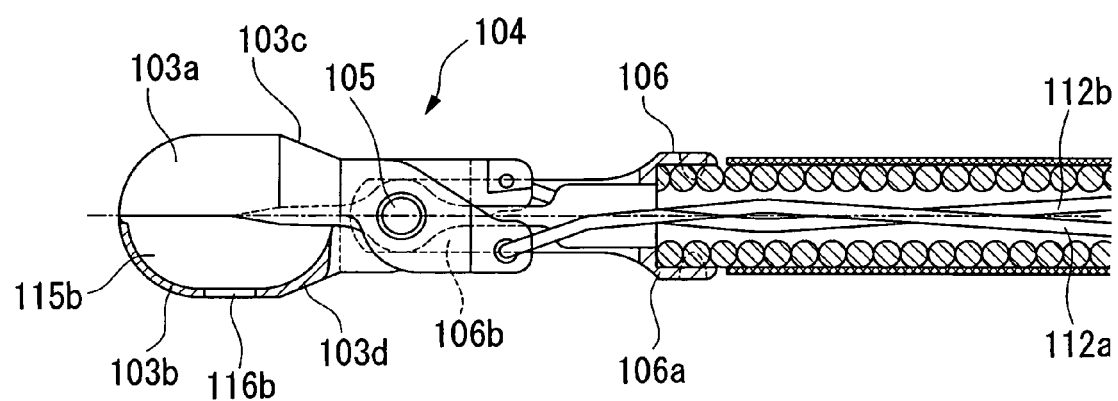
FIG. 11 is a side cross-sectional view showing another example of a treatment tool distal end section of the same treatment tool for an endoscope.

The treatment tool distal end section 104 may be configured as shown in FIG. 10 and FIG. 11. That is, distal ends of operating wires 112a and 112b which are made of two wires may be directly joined to end portions of the rearward-extending arms of each of the biopsy cups 103a and 103b. In addition, an external diameter Da of the biopsy cups 103a and 103b may be larger than a diameter d1a of the supporting body 106. Furthermore, taper sections 103c and 103d may be formed at the rear end sides of the biopsy cups 103a and 103b.

The biopsy cups 103a and 103b have accommodating portions 115a and 115b for accommodating collected tissues. Furthermore, holes 116a and 116b are provided at bottoms of the accommodating portions 115a and 115b of the biopsy cups 103a and 103b so as not to crush the tissues when cutting the tissues.

As shown in FIG. 8, a second finger-receiving section (a second driving-operation section) 117 which is engageable with fingers of an operator of an endoscope is fixed onto a bottom section 102a which is provided on the bottom side of the flexible sheath 102, so as to be arranged besides the flexible sheath 102 and the bottom section 102a. A penetration hole through which a center axis 119a passes is formed within the second finger-receiving section 117. Within this penetration hole, a slider (a first driving-operation section) 118 is inserted so as to be slidably moved along the center axis 119a. In addition, the whole of a cylinder portion of this second finger-receiving section 117 forms a sandwiched portion 117a which is to be held by sandwiching it with a first finger and a second finger when operating this biopsy forceps 101. One end of the turning member 114 is inserted within the bottom section 102a so as to be freely slidable. In addition, the turning member 114 connects between a rear end of the operating wire 112 joined to one end thereof, and the slider 118. An operating section 119 is configured by the second finger-receiving section 117 and the slider 118. The center axis 119a of the operating section 119 is parallel to a center axis C1a of the flexible sheath 102. Accordingly, by performing advancing and retracting operations of the slider 118, opening and closing of the forceps cups 103a and 103b can be performed via the turning member 114 and the operating wire 112.

The slider 118 is provided with: a finger-receiving ring (a thumb-receiving section) 120 provided on the distal end side thereof; and an extending portion 121 which extends rearward from the finger-receiving ring 120, and is inserted within the second finger-receiving section 117. This extending portion 121 may be omitted. That is, the turning member 114 may be directly connected to the finger-receiving ring 120 by extending the turning member 114.

Hereinafter, how to operate the biopsy forceps 101 of the present embodiment having a configuration explained in the above will be explained.

Figure 12:
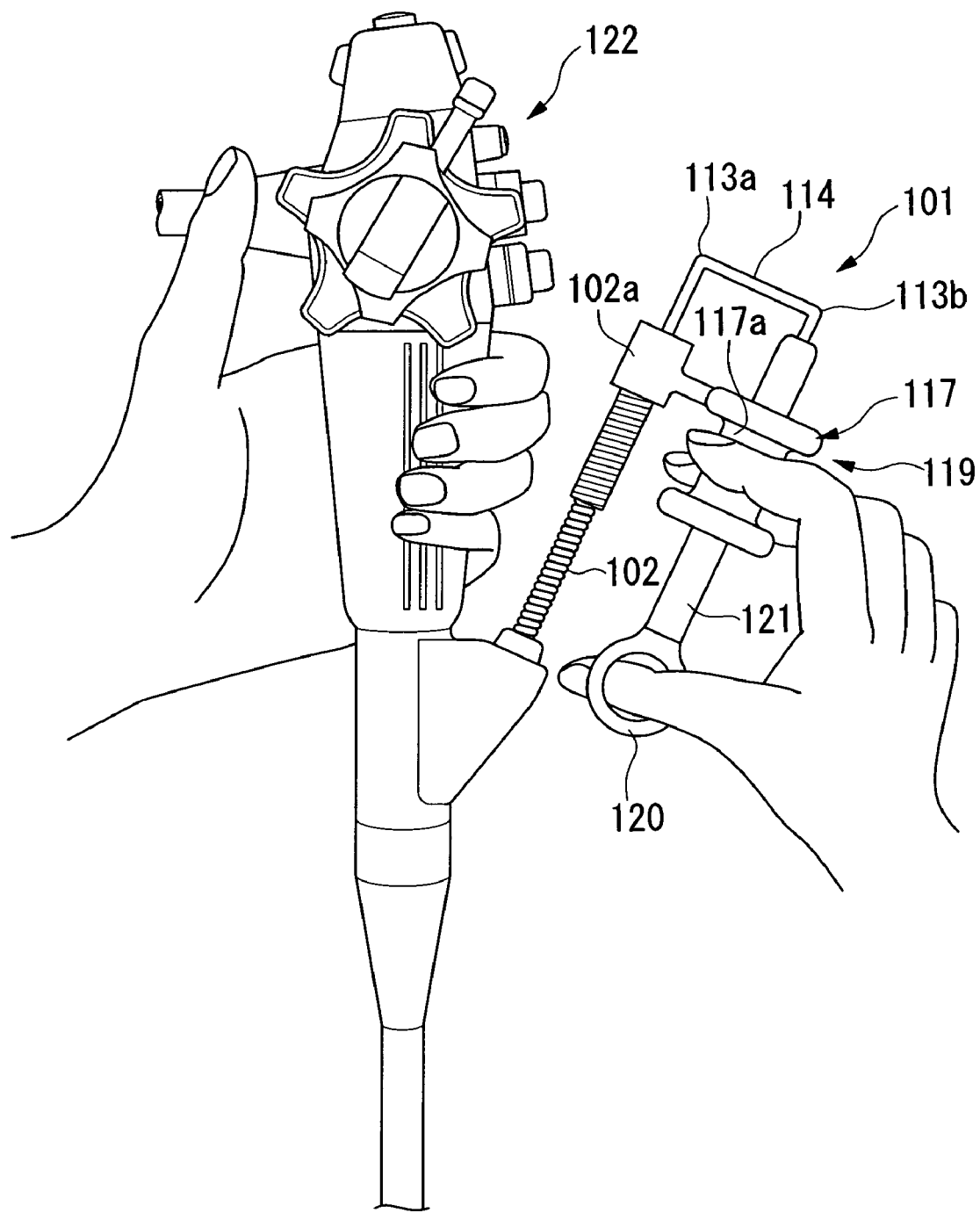
FIG. 12 is a drawing explaining how to operate the same treatment tool for an endoscope, and is also a drawing explaining how to operate when advancing and retracting the treatment tool distal end section.

Firstly, as shown in FIG. 12, the biopsy forceps 101 is inserted into a forceps channel of an endoscope 122. Then, while observing through the endoscope 122, the treatment tool distal end 104 provided at a distal end of the biopsy forceps 101 is moved closer to tissues that should be inspected. An operator of the endoscope 122 will sandwich the second finger-receiving section 117 with his or her first finger and the second finger, while inserting his or her thumb into the finger-receiving ring 120 of the slider 118. Then, the slider 118 is forwarded (i.e., the finger-receiving ring 120 is moved toward the direction departing from the second finger-receiving section 117). Then, the turning member 114 of which another end thereof is fixed to the slider 118 moves together with the slider 118; thereby, advancing the operating wire 112. As a result, the pantagraph mechanism 107 (refer to FIG. 9) works, and thereby opens between the biopsy cups 103a and 103b. Next, while the biopsy cups 103a and 103b are opened, the biopsy forceps 101 is pressed towards the tissues. Then, when retracting the slider 118, the operating wire 112 will be retracted by the turning member 114 which retracts together with the slider 118. As a result, the forceps cups 103a and 103b are closed, and the tissues are accommodated into the accommodating portions 115a and 115b of the forceps cups 103a and 103b. Then, when the forceps cups 103a and 103b are completely closed, the biopsy forceps 101 will be removed from the forceps channel of the endoscope 122 by pulling the whole of the biopsy forceps 101; thereby, completing collection of the tissues.

According to the above-explained biopsy forceps 101 of the present embodiment, when an operator of the endoscope 122 grips and operates the operating section 119, it is possible to arrange his or her thumb at the lower side of the operating section 119 and to arrange his or her first finger and second finger at the upper side of the operating section 119, without reversing the direction of the operating section 119. That is, there is no possibility of causing damage to the flexible sheath 102 due to the reversing of the operating section 119. In addition, the operating section 119 can be gripped without any difficulties since the operator has no necessity to bend his or her hand toward an unnatural direction; thereby, enabling easy operations of the operating section 119. Furthermore, motions of the fingers (i.e., closing and departing motions between a thumb, and a first finger and a second finger) become the same as the conventional ones; therefore, the motions of the fingers and motions of the treatment tool distal end section 104 become the same, thereby preventing any awkward feeling by the operator.

Figure 13:
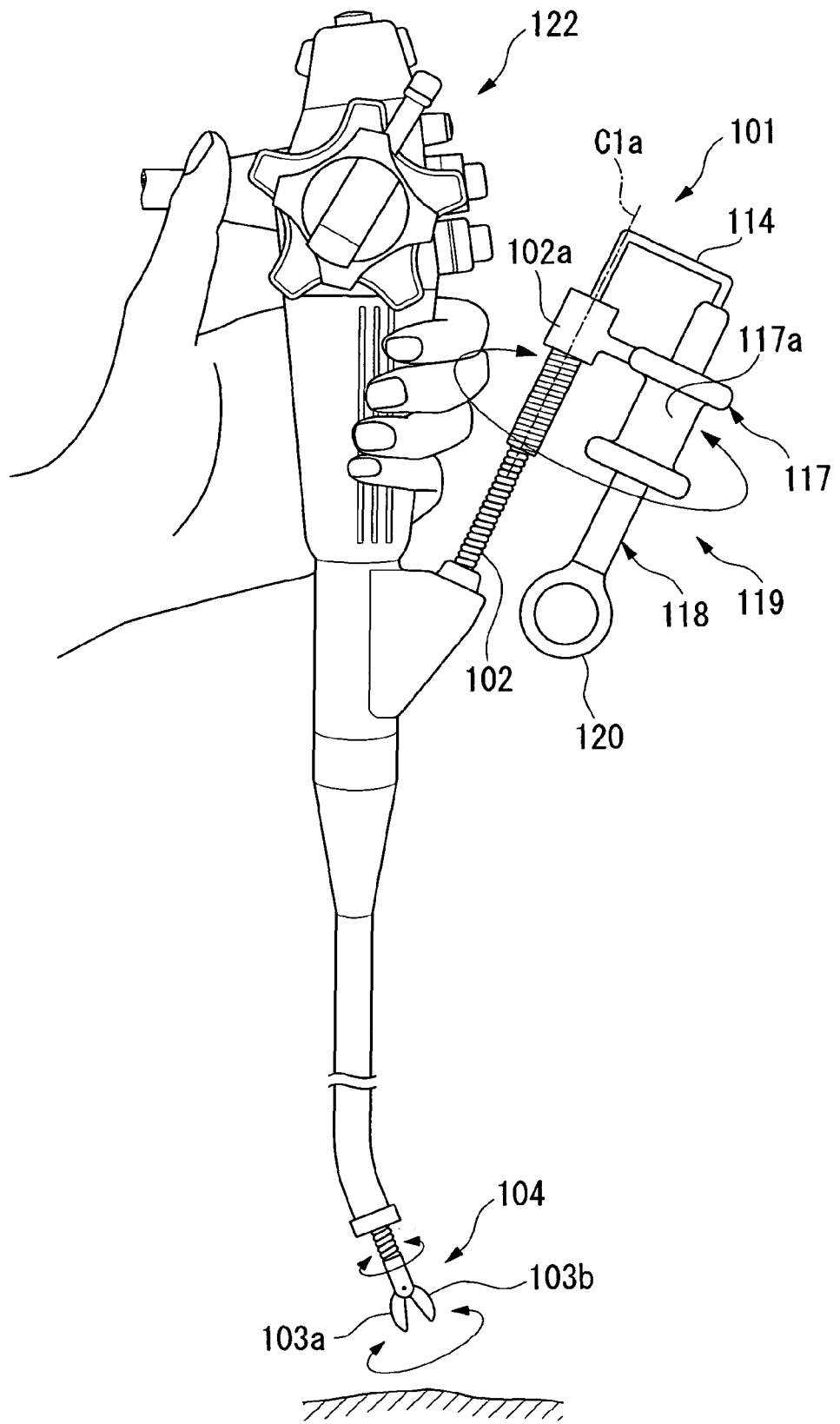
FIG. 13 is a drawing explaining how to operate the same treatment tool for an endoscope, and is also a drawing explaining how to operate when rotating the treatment tool distal end section.

Moreover, as shown in FIG. 13, when adjusting the rotational directions of the forceps cups 103a and 103b while these forceps cups 103a and 103b are opened, the whole of the operating section 119 will be rotated around a center axis C1a of the flexible sheath 102. Then, the treatment tool distal end section 104 can be easily rotated via the flexible sheath 102.

Fourth Embodiment

Next, a fourth embodiment of a treatment tool for an endoscope of the present invention will be explained with reference to FIG. 14 to FIG. 17. Moreover, through the explanation of the present embodiment, the same reference symbols will be applied to the same configuration elements as the ones explained in the above-mentioned third embodiment, and the explanations thereof will be omitted here.

Figure 14:
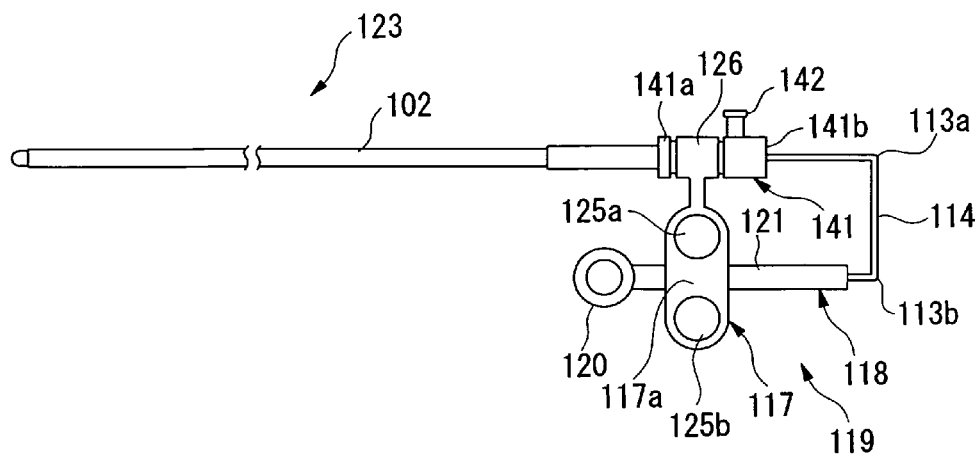
FIG. 14 is a side view showing a configuration of a treatment tool for an endoscope according to a fourth embodiment of the present invention.
Figure 15:
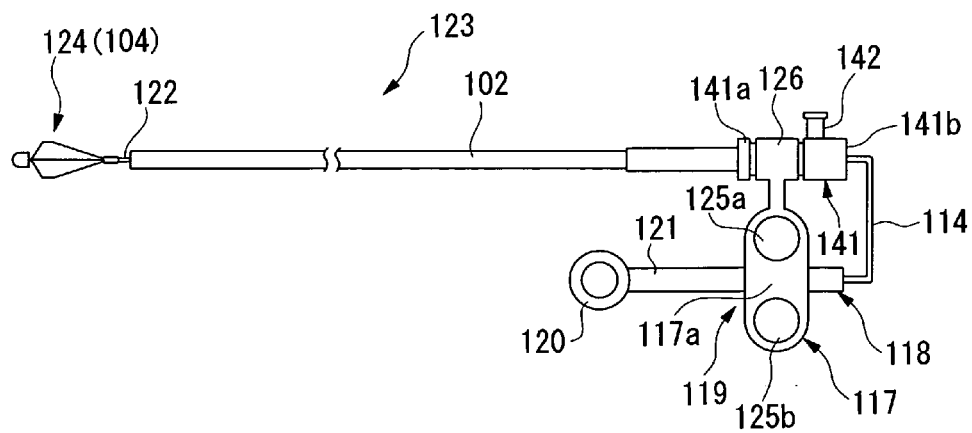
FIG. 15 is a drawing showing the same treatment tool for an endoscope, and also showing the state in which a treatment tool distal end section is advanced.

As shown in FIG. 14 and FIG. 15, a basket-type clamp forceps (a treatment tool for an endoscope) 123 is provided with a basket portion 124 which serves as the treatment tool distal end section 104 provided on a distal end of the operating wire 112. Two finger-receiving holes 125a and 125b are formed within the second finger-receiving section 117. In addition, a sandwiched section 117a which is to be sandwiched between a first finger and a second finger when the basket-type clamp forceps 123 is operated, is provided between these finger-receiving holes 125a and 125b. The second finger-receiving section 117 is rotatably connected to a bottom section 141 which is fixed to the bottom end of the flexible sheath 102, via a rotational joint section 126. Other configurations except these are the same as the ones of the above-mentioned third embodiment.

The bottom section 141 has a substantial cylinder-shape, and a rear end of the operating wire 112 and one end of the turning member 114 are inserted therein. The rotational joint section 126 having a substantial cylinder-shape is rotatably connected to the periphery of the bottom section 141. Two projections 141a and 141b which are formed by projecting the external diameter of the bottom section 141 toward the exterior in the diameter direction, prevent sliding operations along the axis line C1a (refer to FIG. 17) of the rotational joint section 126. The projection 141b is provided with a mouthpiece 142 for providing a contrast medium or the like into the flexible sheath 102.

Hereinafter, how to operate the basket-type clamp forceps 123 having the above-explained configuration will be explained.

Figure 16:
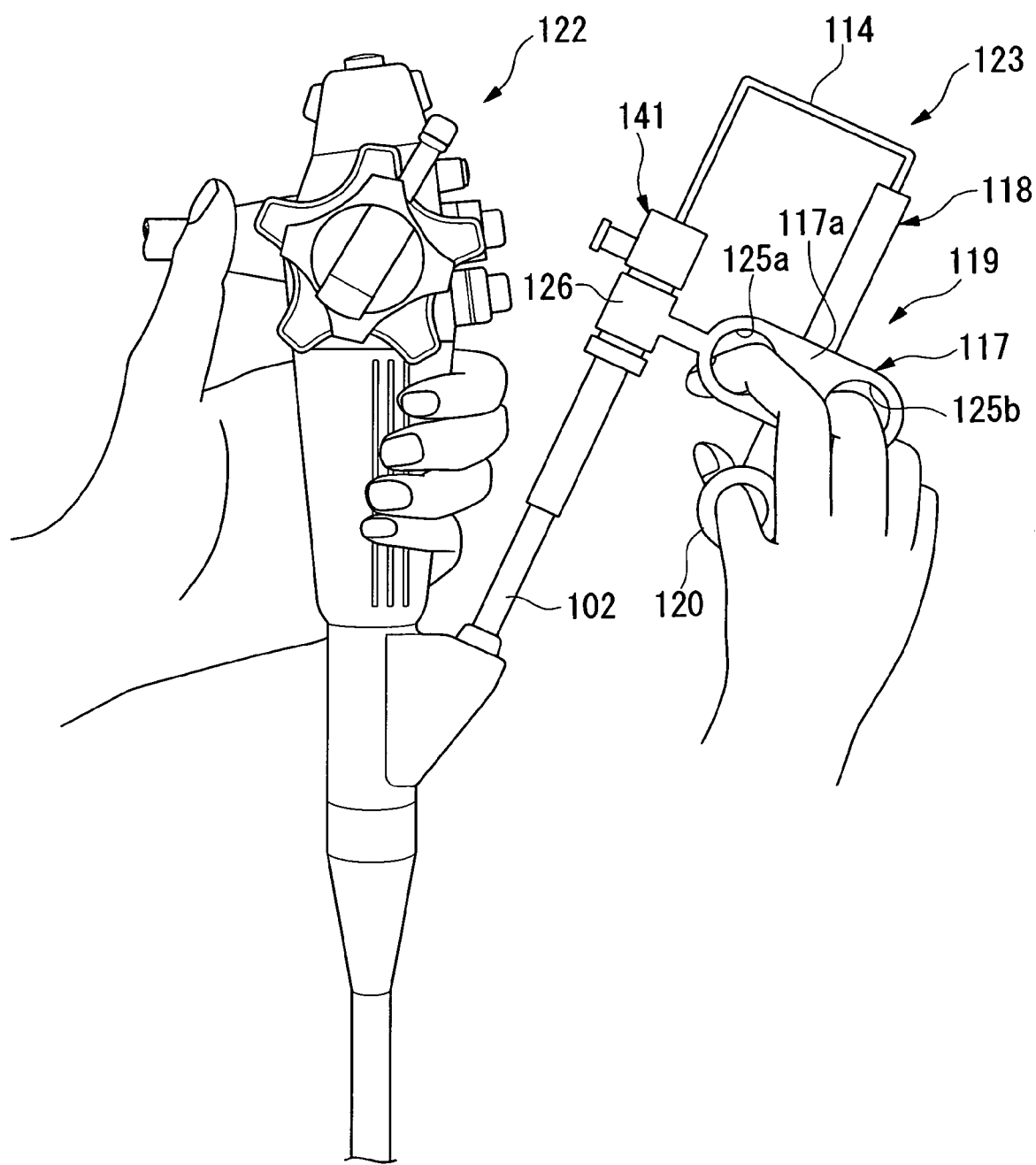
FIG. 16 is a drawing explaining how to operate the same treatment tool for an endoscope.

Firstly, as shown in FIG. 16, the basket-type clamp forceps 123 is inserted into the forceps channel of the endoscope 122. Then, while observing through the endoscope 122, the distal end of the basket-type clamp forceps 123 is moved closer to a target portion. Then, an operator of the endoscope 122 will engage his or her first finger and second finger with the finger-receiving holes 125a and 125b of the second finger-receiving section 117 so as to sandwich the sandwiched section 117a therebetween. Furthermore, the operator will insert his or her thumb into the finger-receiving ring 120 of the slider 118, and will engage the thumb therewith. Then, the slider 118 will be advanced (i.e., the finger receiving ring 120 will be moved toward the direction departing from the second finger-receiving section 117). Then, the turning member 114 will be advanced together with the operating wire 112, and the basket portion 124 will be protruded from the distal end of the flexible sheath 102 and open. Then, after taking a collected object into the basket portion 124, the slider 118 will be retracted; thereby, closing the basket portion 124 and reliably capturing the collected object. Thereafter, the operation will be ended by removing the basket-type clamp forceps 123 together with the endoscope 122 from the body cavity.

According to the basket-type clamp forceps 123 of the present embodiment explained in the above, the same advantages as the ones of the above-mentioned third embodiment can be obtained.

Figure 17:
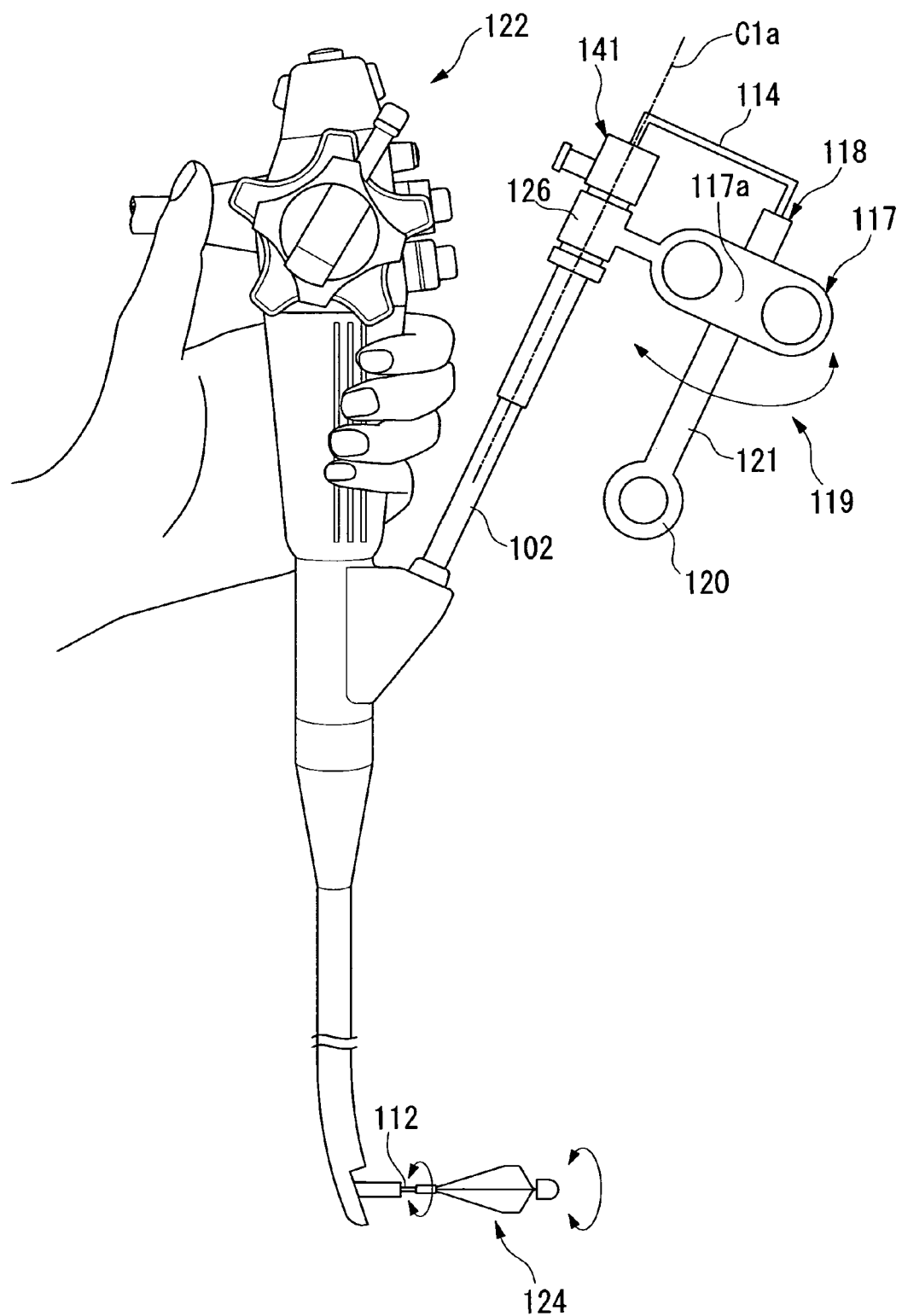
FIG. 17 is a drawing explaining how to operate the same treatment tool for an endoscope, and also explaining how to operate when rotating the treatment tool distal end section.

Moreover, as shown in FIG. 17, in order to adjust the direction of the basket portion 124 while it is opened, the whole of the operating section 119 is rotated around the center axis C1a of the flexible sheath 102 and the bottom section 141; thereby, enabling easy rotations of the basket portion 124 via the operating wire 112.

Fifth Embodiment

Next, a fifth embodiment of a treatment tool for an endoscope of the present invention will be explained with reference to FIG. 18 to FIG. 20. Moreover, through the explanation of the present embodiment, the same reference symbols will be applied to the same configuration elements as the ones explained in the above-mentioned third and fourth embodiments, and the explanations thereof will be omitted here.

Figure 18:
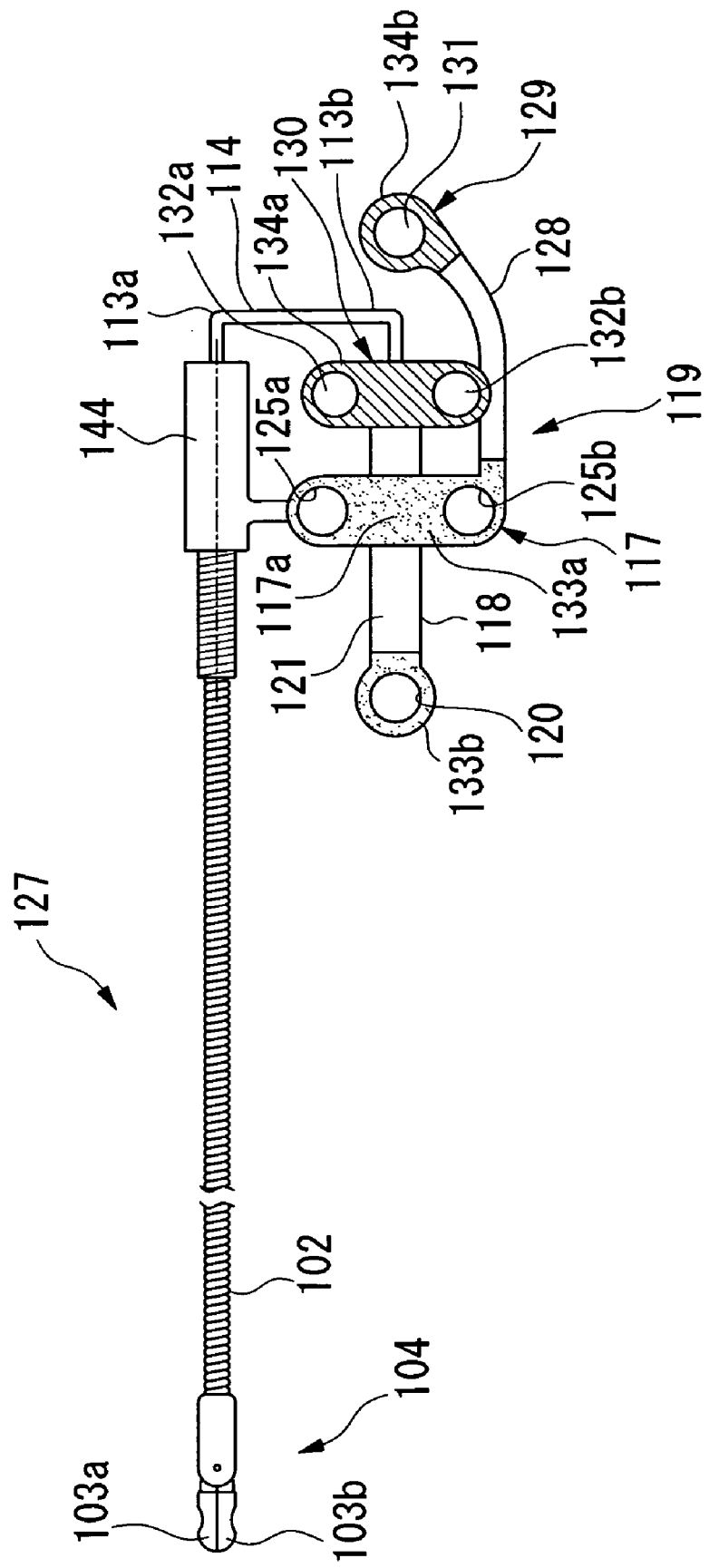
FIG. 18 is a drawing showing a configuration of a treatment tool for an endoscope according to a fifth embodiment of the present invention.

As shown in FIG. 18, an operating section 119 of a biopsy forceps 127 of the present embodiment differs from the one of the above-mentioned third embodiment. The second finger-receiving section 117 of the present embodiment is provided with a supporting member 128 which extends towards the bottom end direction. A third finger-receiving section (a third driving-operation section) 129 is formed at a rear end of the supporting member 128. In addition, a fourth finger-receiving section (a fourth driving-operation section) 130 is provided at a rear end of an extending portion 121 of the slider (a second driving-operation section) 118. The fourth finger-receiving section 130 is disposed between the second finger-receiving section 117 and the third finger-receiving section 129. One finger-receiving hole 131 is provided within the third finger-receiving section 129 while two finger-receiving holes 132a and 132b are provided within the fourth finger-receiving section 130, so as to be engageable with the fingers of a care assistant.

In the first to fourth finger-receiving sections 118, 117, 129, and 130, at least a part thereof is colored. That is, a colored portion 133a of the second finger-receiving section 177 and a colored portion 133b of the slider (a second driving-operation section) 118 are colored the same color as each other. In addition, a colored portion 134a of the third finger-receiving section 129 and a colored portion 134b of the fourth finger-receiving section 130 are colored the same color as each other. Furthermore, the portions 133a and 133b, and the colored portions 134a and 134b are colored in different colors from each other.

Furthermore, the second finger-receiving section 117 of the present embodiment is fixed to a cylinder-shaped bottom section 144 fixed to the bottom end of the flexible sheath 102. Other configurations except for the above are the same as the one of the above-mentioned third embodiment.

Hereinafter, how to operate the biopsy forceps 127 of the present embodiment, which has the above-explained configurations, will be explained.

Figure 19:
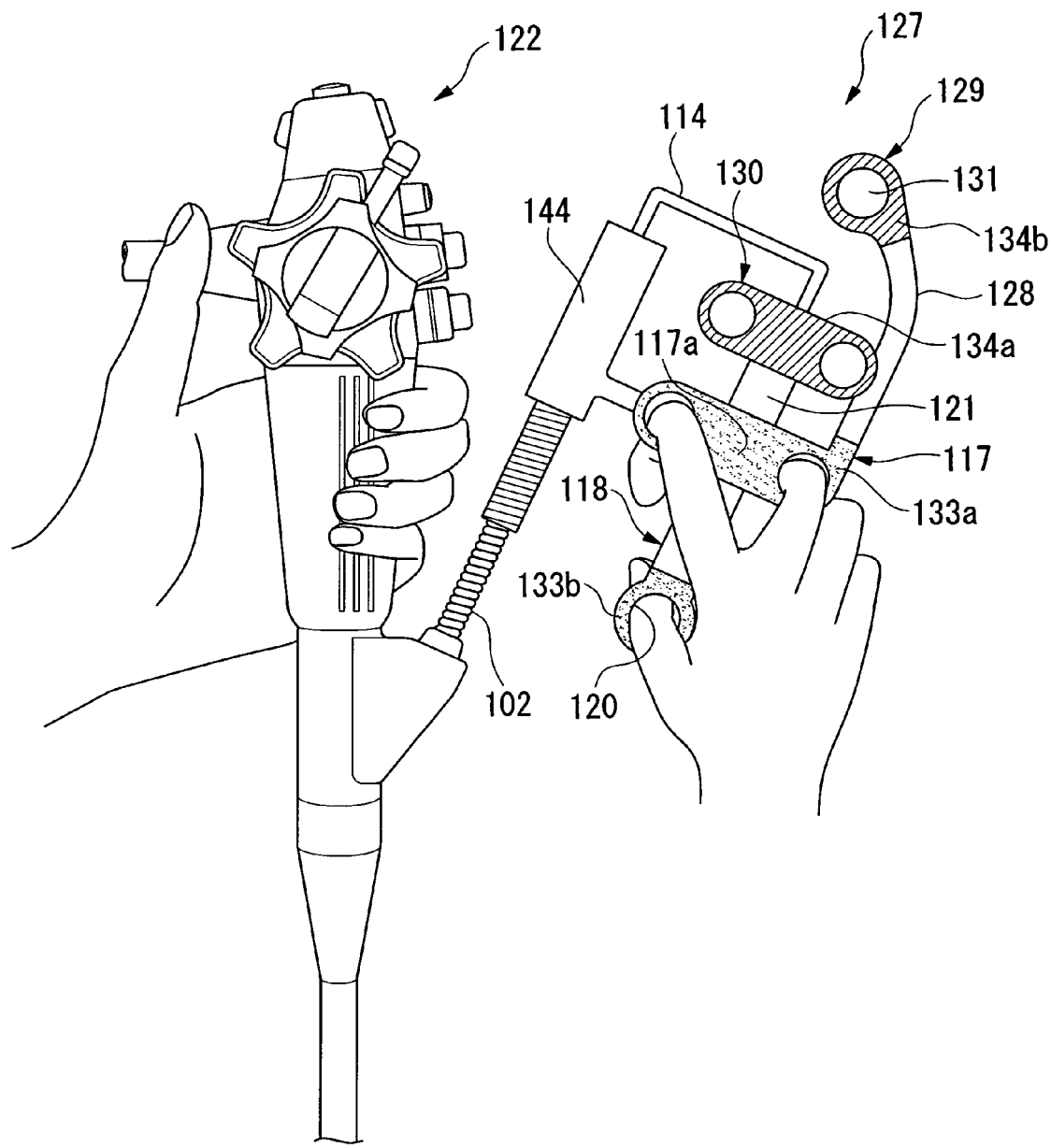
FIG. 19 is a drawing explaining how to operate the same treatment tool for an endoscope, and also showing the case in which an operator operates the endoscope.

Firstly, when an operator of the endoscope 122 operates, as shown in FIG. 19, using the second finger-receiving section 117 having the portions 133a and 133b which are colored in the same color, and the slider 118, an operation is performed in the same manner as is in the above-mentioned third embodiment.

Figure 20:
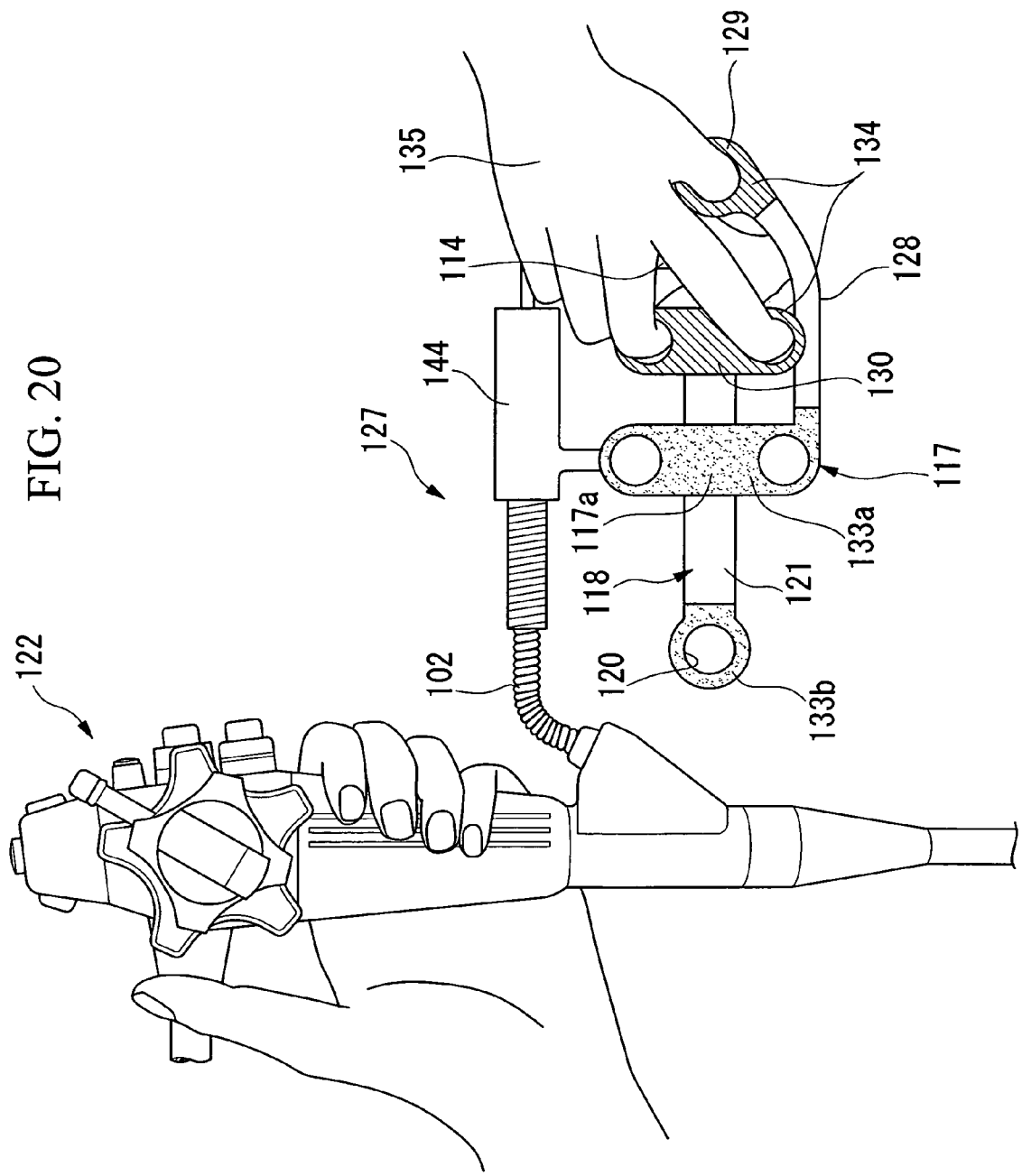
FIG. 20 is a drawing explaining how to operate the same treatment tool for an endoscope, and also showing the case in which a care assistant operates.

In addition, as shown in FIG. 20, when a care assistant 135 standing beside the operator of the endoscope, the third finger-receiving section 129 having the portions 134a and 134b which are colored in the same color, and the fourth finger-receiving section 130 will be used.

That is, the care assistant 135 inserts his or her thumb into the finger-receiving hole 131 of the third finger-receiving section 129 while inserting his or her first finger and second finger into the holes 132a and 132b of the fourth finger-receiving section 130, and thereafter advances and retracts the slider 118. That is, when the fourth finger-receiving section 130 is operated so as to move away from the third finger-receiving section 129, the operating wire 112 which is joined to the fourth finger-receiving section 130 through the turning member 114, will be advanced; thereby, opening the forceps cups 103a and 103b. In this state, by operating the fourth finger-receiving section 130 so as to be moved closer to the third finger-receiving section 129, the operating wire 112 will be retracted via the turning member 114; thereby, closing the forceps cups 103a and 103b.

According to the biopsy forceps 127 of the present embodiment explained in the above, when the operator of the endoscope 122 grips and operates, the same advantages as the ones in the above-mentioned third embodiment will be obtained. In addition, when the care assistant 135 standing beside the operator of the endoscope operates, it is also possible to perform easy operations in the same manner since he or she can grip without any difficulties. In addition, motions for opening and closing the forceps cups 103a and 103b (i.e., departing and closing motions between a thumb, and a first finger and a second finger) are the same as the conventional ones in each case; therefore, preventing any awkward feeling by the operator of the endoscope and by the care assistant 135.

In addition, since portions that should be gripped by the operator of the endoscope and the care assistant 135 (i.e., a combination of the portion 133a and the portion 133b, and a combination of the portion 134a and the portion 134b) are colored in the different colors (a distinguishing means) so as to be able to confirm them by sight, the portions that should be gripped are clear and there is no possibility of making mistakes.

Sixth Embodiment

Figure 21:
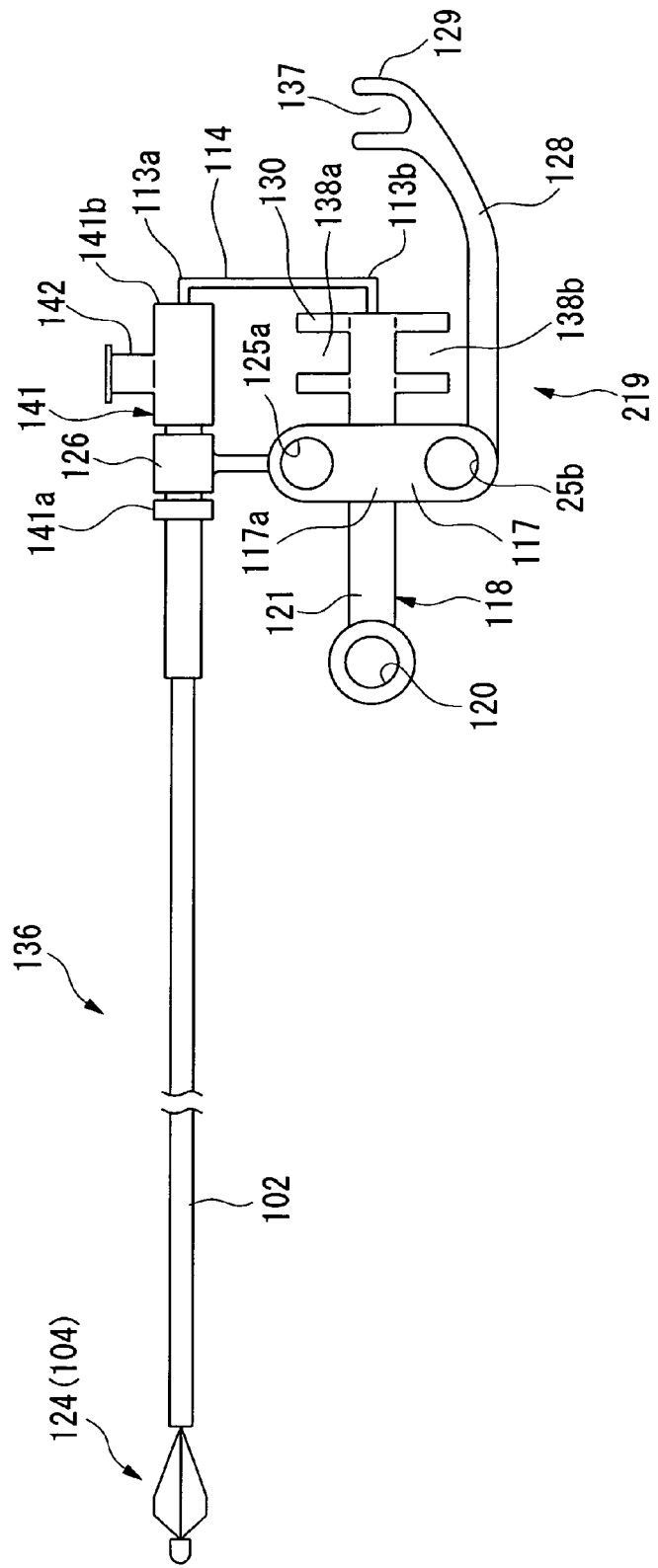
FIG. 21 is a side view showing a configuration of a treatment tool for an endoscope according to a sixth embodiment of the present invention.

Next, a sixth embodiment of a treatment tool for an endoscope of the present invention will be explained with reference to FIG. 21. Moreover, through the explanation of the present embodiment, the same reference symbols will be applied to the same configuration elements as the ones explained in the above-mentioned third to fifth embodiments, and the explanations thereof will be omitted here.

In a basket-type clamp forceps (a treatment tool for an endoscope) 136 of the present embodiment, a third finger-receiving section 129 of an operating section 219 (in order to distinguish it from the above-mentioned operating section 119, new reference symbol 219 will be applied) and finger-receiving sections 137, 138a, and 138b of a fourth finger-receiving section 130, are different from the above-mentioned fifth embodiment. That is, in the present embodiment, each of the finger-receiving section 137 of the third finger-receiving section 129, and the finger-receiving sections 138a and 138b of the fourth finger-receiving section 130 has a shape which opens towards one direction. For example, each of the finger-receiving sections 137, 138a, and 138b is formed in a shape opened towards a direction substantially orthogonal to the advancing and retracting directions of the treatment tool distal end section 104. Configurations of the operating section 119 except for the above are the same as the ones of the above-mentioned fifth embodiment. In addition, configurations other than the operating section 119 are the same as the ones of the above-mentioned fourth embodiment.

According to the basket-type clamp forceps 136 of the present embodiment explained in the above, the same advantages can be obtained as the ones of the above-mentioned fifth embodiment. In the present embodiment, distinction can be made by the shapes (a distinguishing means) of portions to be engaged by fingers, while, in the fifth embodiment, distinction between a portion that should be gripped by the operator of the endoscope and a portion that should be gripped by the care assistant 135 is made by the colors 133 and 134. That is, in the present embodiment, when the operator of the endoscope operates, the basket-type clamp forceps 136 will be operated by inserting his or her fingers into the three ring-shaped finger-receiving sections (i.e., the finger-receiving ring 120, the finger-receiving holes 125a and 125b) each having similar shape. On the other hand, when the care assistant operates, the basket-type clamp forceps 136 will be operated by engaging his or her fingers with the three finger-receiving sections 137, 138a, and 138b, each having a similar shape and opening at an end portion thereof.

Seventh Embodiment

Next, a seventh embodiment of a treatment tool for an endoscope of the present invention will be explained with reference to FIGS. 22 to 24. Moreover, through the explanation of the present embodiment, the same reference symbols will be applied to the same configuration elements as the ones explained in the above-mentioned fourth embodiments, and the explanations thereof will be omitted here.

Figure 22:
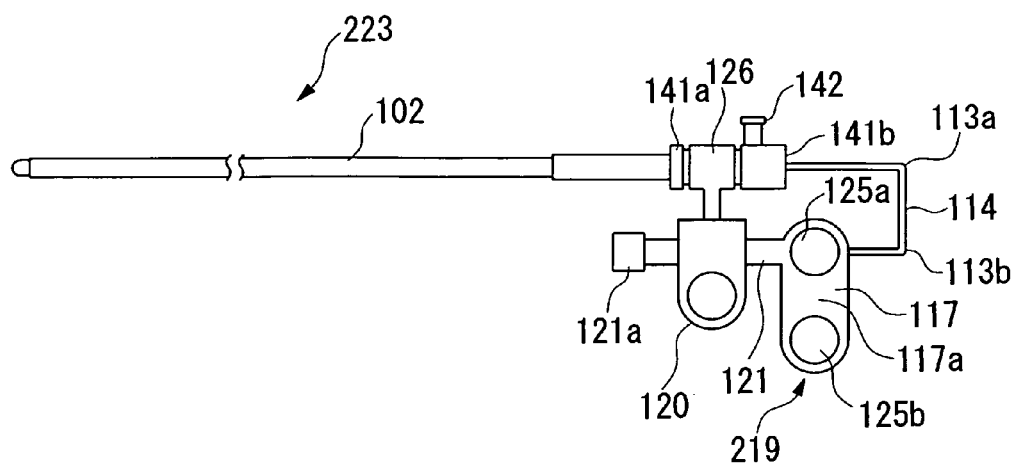
FIG. 22 is a side view showing a configuration of a treatment tool for an endoscope according to a seventh embodiment of the present invention.
Figure 23:
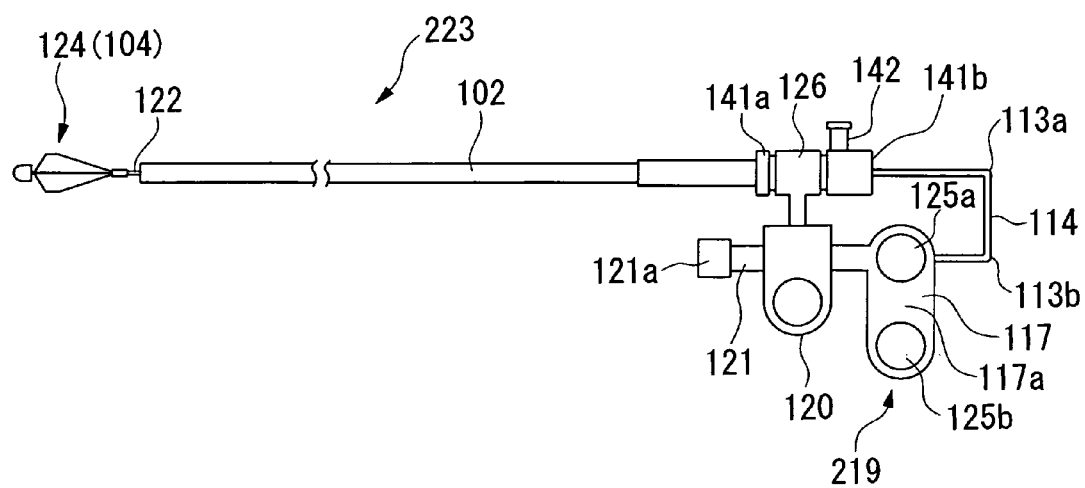
FIG. 23 is a side view showing the same treatment tool for an endoscope, and also showing the state in which a basket portion is opened.

As shown in FIG. 22 and FIG. 23, a basket-type clamp forceps (a treatment tool for and endoscope) 223 of the present embodiment differs from the basket-type clamp forceps 223 of the above-mentioned fourth embodiment in that the present embodiment adopts a configuration of performing operations by moving the second finger-receiving section 117 side with respect to the relatively static finger-receiving ring 120, while the fourth embodiment adopts a configuration of performing operations by moving the finger-receiving ring 120 side with respect to the relatively static second finger-receiving section 117.

That is, in the present embodiment, instead of the second finger-receiving section 117, the finger-receiving ring 120 is fixed to the rotational joint section 126. In addition, instead of the extending portion 121, the second finger-receiving section 117 is joined to the turning member 114. The finger-receiving ring 120 of the present embodiment has a penetration hole formed therein, which extends along the advancing and retracting direction of the turning member 114. In addition, the extending portion 121 is joined to the second finger-receiving section 117 so as to form one unit therewith. Furthermore, this extending portion 121 is inserted within the above-mentioned penetration hole of the finger-receiving ring 120 so as to be slidable along the advancing and retracting directions of the turning member 114. Moreover, the reference symbol 121a denotes a stopper for preventing the extending portion 121 being removed from the above-mentioned penetration hole of the finger-receiving ring 120. Furthermore, configurations other than the operating section 219 are the same as the ones of the above-mentioned fourth embodiment.

Hereinafter, how to operate the basket-type clamp forceps 223 of the present embodiment, which has the above-explained configurations, will be explained.

Figure 24:
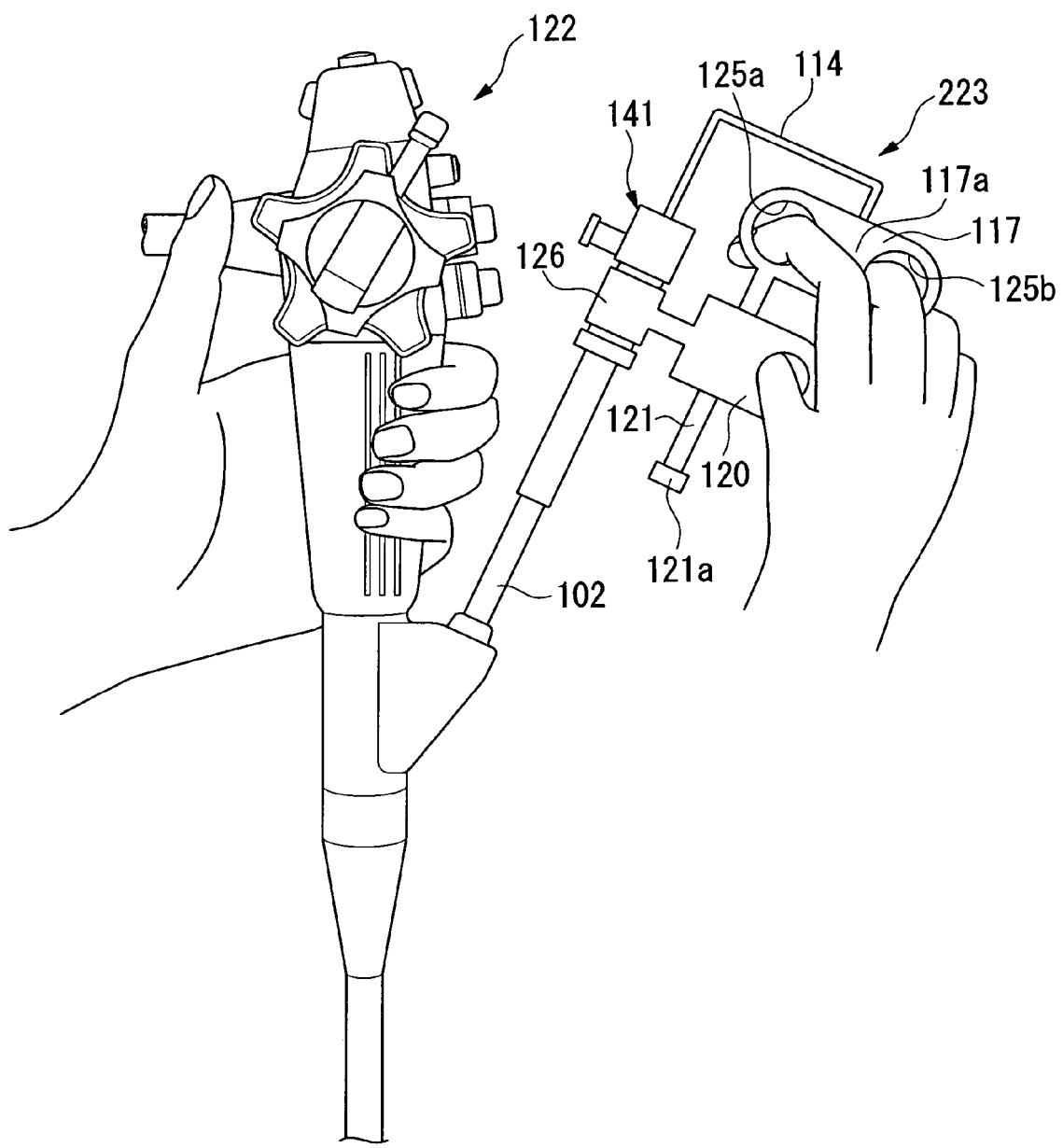
FIG. 24 is a drawing explaining how to operate the same treatment tool for an endoscope.
Figure 25:
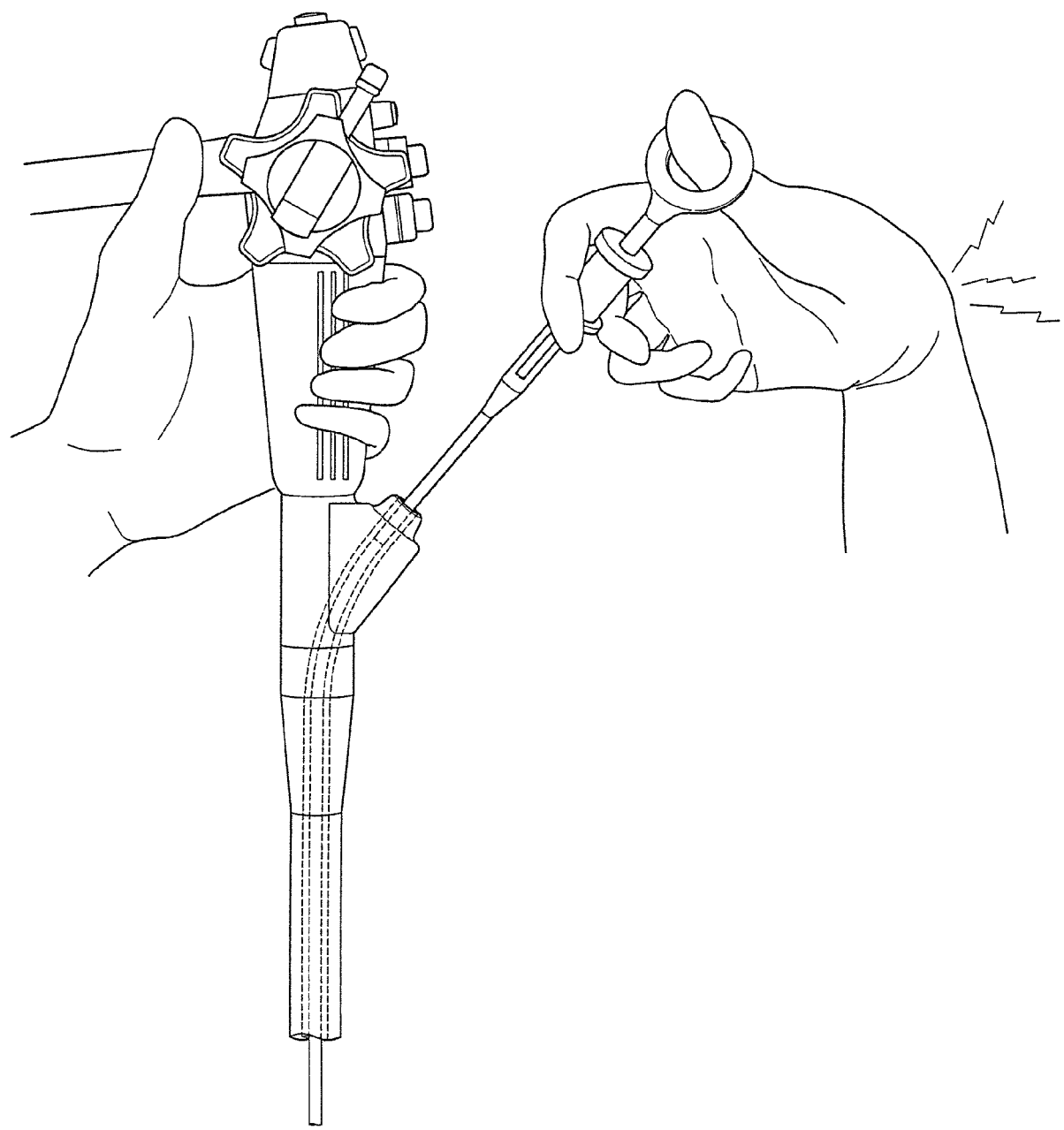
FIG. 25 is a drawing explaining how to operate a conventional treatment tool for an endoscope.
Figure 26:
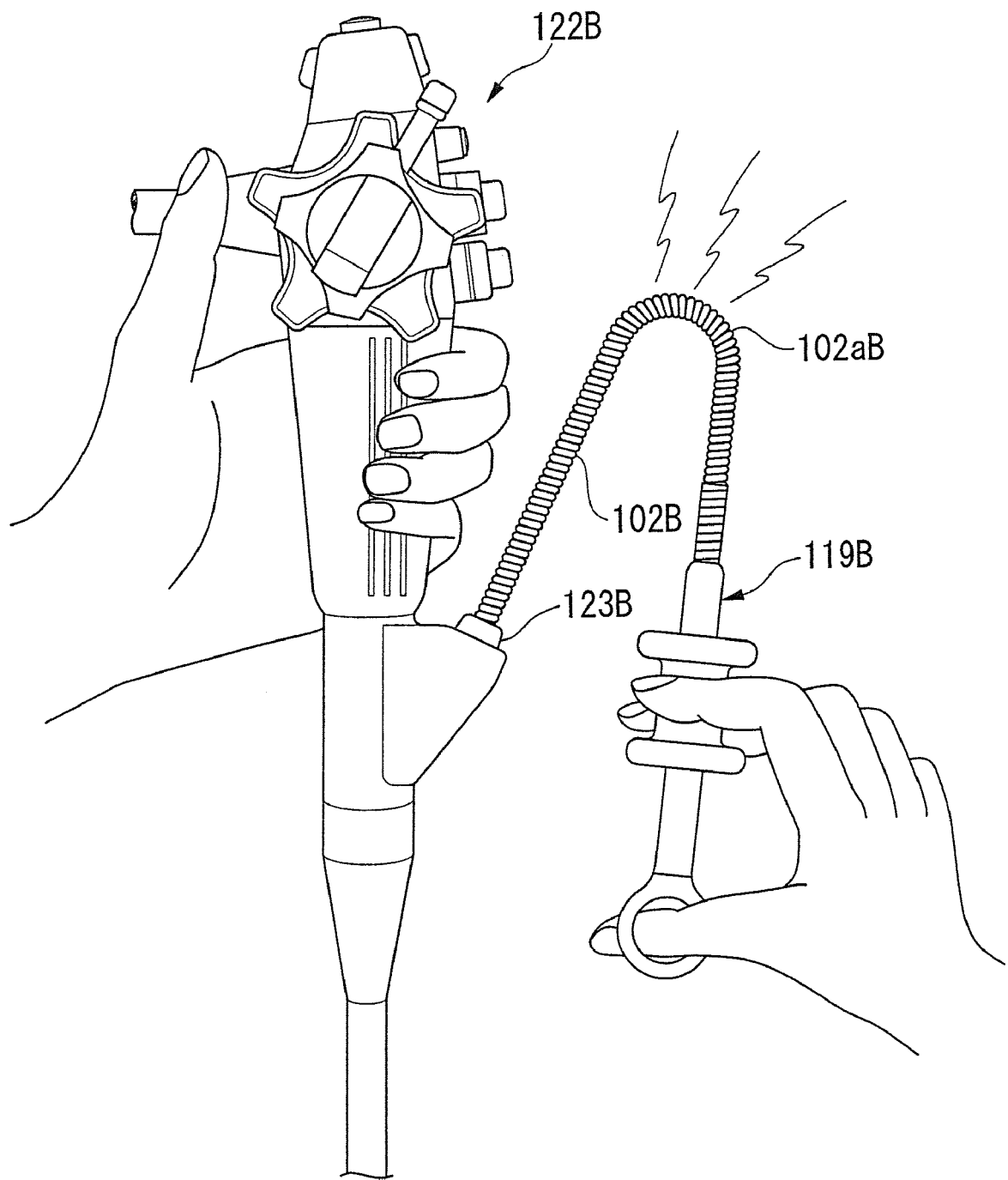
FIG. 26 is a drawing explaining how to operate another conventional treatment tool for an endoscope.

Firstly, as shown in FIG. 24, the basket-type clamp forceps 223 is inserted into the forceps channel of the endoscope 122. Then, while observing through the endoscope 122, the distal end of the basket-type clamp forceps 223 is moved closer to a target portion. Then, an operator of the endoscope 122 will insert his or her first finger and second finger into the finger-receiving holes 125a and 125b and will engage therewith, so as to sandwich the sandwiched section 117a therebetween. Furthermore, the operator will insert his or her thumb into the finger-receiving ring 120 and will engage the thumb therewith. Then, the second finger-receiving section 117 will be advanced (i.e., the second finger-receiving section 117 will be moved toward the direction closer to the finger-receiving ring 120). Then, the turning member 114 will be advanced together with the operating wire 112, and the basket portion 124 will be protruded from the distal end of the flexible sheath 102 and open. Then, after taking a collected object into the basket portion 124, the second finger-receiving section 117 will be retracted; thereby, closing the basket portion 124 and reliably capturing the collected object. Thereafter, the operation will be ended by removing the basket-type clamp forceps 223 together with the endoscope 122 from the body cavity.

According to the basket-type clamp forceps 223 of the present embodiment explained in the above, the same advantages can be obtained as the ones of the above-mentioned fourth embodiment.

As has been explained in the above, the present invention adopts the following.

A treatment tool for an endoscope of the present invention includes: an operating duct section which is to be inserted into a forceps channel of the endoscope; a treatment tool distal section which is provided on a distal end side of this operating duct section; and an operating section which is provided on a bottom end side of the operating duct section, wherein: the operating duct section includes an operating wire of which one end is joined to the treatment tool distal end; and the operating section includes a pair of driving-operation sections which advance and retract the operating wire by relative closing-and-departing motions thereof; and wherein: one of the pair of driving-operation sections is provided with a first finger-receiving section to which a finger which operates the operating section is engaged, while the other is provided with a second finger-receiving section which has a sandwiched section to be sandwiched between the other fingers, and onto which the other fingers are to be engaged; and an arrangement thereof is made such that, when the operating duct section is inserted within the forceps channel, a distance from the second finger-receiving section to an opening of the forceps channel on the operating section side of the endoscope becomes longer than a distance from the first finger-receiving section to the opening of the forceps channel, on the operating section side of the endoscope.

According to the above-mentioned treatment tool for an endoscope, by inserting the operating duct section into the forceps channel of the endoscope, the operating section can simply be mounted such that the second finger-receiving section is disposed at a position higher than the first finger-receiving section in the vertical direction. And the thumb is engaged with the first finger-receiving section, while the other fingers (for example, two of a first finger and a second finger) are engaged with the second finger-receiving section by sandwiching the sandwiched section therebetween. Under this state, by closing and departing the thumb and the other fingers against each other, the first finger-receiving section and the second finger-receiving section will be closed to and departed from each other; thereby, enabling operations of the treatment tool distal end section through the operating wire. At this time, the other fingers (for example, two of a first finger and a second finger) engaged with the second finger-receiving section are disposed at a position higher, in the vertical direction, than the thumb engaged with the first finger-receiving section; therefore, operations of the operation section can be made without twisting a wrist while a hand is simply raised upright, and with a simple and easy posture. Accordingly, the operating section can be easily gripped during treatments, and thereby becomes easy to be operated. With this, burden on a hand of the operator can be decreased; thereby, enabling improvements on the operability of the treatment tool for an endoscope.

It is preferable that the first finger-receiving section is a one hole-section to which a thumb which operates the operating section is engaged.

With this, any mistake in the direction of a hand (i.e., up and down directions) when holding the operating section can be reliably prevented.

It may be arranged such that: the operating duct section is flexible; and the operating section includes a hard joint-section which connects this operating section onto a forceps opening of the forceps channel so as to make it stand thereon.

In this case, it is possible to secure stable operations while the operating section is mounted so as to stand on the forceps opening.

It may be arranged such that one of the pair of driving-operation sections, on a movable side, and another end of the operating wire are joined via a turning member having hardness and a substantial U-shape.

In this case, there is no possibility of causing damage to the operating duct section due to severe bending applied onto the operating duct section, or deteriorating movements of the operating wire.

It may be arranged such that a bottom end of the operating wire is joined to the first finger-receiving section.

It may be arranged such that a bottom end of the operating wire is joined to the second finger-receiving section.

A treatment tool for an endoscope of the present invention includes: an operating duct section which is to be inserted into a forceps channel through a forceps opening of the endoscope; a treatment tool distal section which is joined to a distal end side of this operating duct section; and an operating section which is joined to a bottom end side of the operating duct section and operates the treatment tool distal section, wherein: the operating duct section includes an operating wire which drives the treatment tool distal section; the operating section includes: a body of which one end is joined to a bottom end of the operating duct section, and stands on the forceps opening while the operating duct section is inserted within the forceps channel; and a slider section which is joined to a bottom end of the operating wire, and is advanceable and retractable between one end and the other end of the body; and the slider section is provided with one first finger-receiving section, while the other end of the body is provided with a second finger-receiving section.

According to this treatment tool for an endoscope, the operating section can be mounted in a manner such that it stands upright without descending from the forceps opening. Meanwhile, since one first finger-receiving section is provided, by engaging this with the thumb and also engaging the other fingers with the second finger-receiving section, it is possible to dispose the thumb and the other fingers respectively at one end side and the other end side of the main body. With this, the treatment tool distal end section can be operated by sliding operations of the slider section between both fingers. At this time, the thumb is disposed at the lower side, while the other fingers are disposed at the upper side. Accordingly, sliding operations of the slider section can be made without twisting a wrist while a hand is simply raised upright, and with a simple and easy posture.

It is preferable that the first finger-receiving section has a shape that is engageable with a thumb, while the second finger-receiving section has a shape that is engageable with the other fingers.

In this case, it is possible, more simply, to engage the thumb with the first finger-receiving section and to engage the other fingers with the second finger-receiving section. Accordingly, sliding operations of the sliding section can be made with an easy posture.

It may be arranged such that: the first finger-receiving section is a thumb hole section through which a thumb is inserted; the second finger-receiving section is one or a plurality of hole sections through which other fingers are inserted; and a linear line connecting between a center of the hole sections and a center of the thumb hole section is parallel to an advancing-and-retracting direction of the slider section.

In this case, operations of the slider section become easy since the thumb and the other fingers can be moved along the sliding direction of the slider section. Furthermore, there is no need to apply wasteful power during the operations; thereby, enabling operations with more easy posture.

It may be arranged such that a distal end of the main body is provided with a hard joint-member which is connected to the forceps channel.

In this case, when the hard joint-member is connected to the forceps channel by inserting it into the forceps opening, the operating section can be fixed with respect to the forceps opening; thereby, enabling operations to be performed in a stable manner.

It may be arranged such that the operating section is provided with an attaching portion which is attached to and is detached from the forceps opening.

In this case, by mounting and fixing the attaching portion onto the forceps opening, the operating section can be provided so as to stand on the forceps opening in a more stable manner.

A treatment tool for an endoscope of the present invention includes: a flexible operating duct section which is to be inserted into a forceps channel through a forceps opening of an endoscope; a treatment tool distal section which is joined to a distal end side of this operating duct section; and an operating section which is joined to a bottom end side of the operating duct section and operates the treatment tool distal section, wherein:

the operating duct section includes an operating wire which drives the treatment tool distal section; and the operating section includes: a first driving-operation section which is supported beside the operating duct section; a second driving-operation section which is provided on a side of the treatment tool distal end section than the first driving-operation section, and advances and retracts with respect to the first driving-operation section; and a turning member which joins between the second driving-operation section and a bottom end of the operating wire, and has hardness and a substantial U-shape.

According to this treatment tool for an endoscope, an operator of an endoscope can grip this treatment tool for an endoscope without causing problems such as damaging the operating duct section due to severe bending applied onto the operating duct section, or deteriorating the movement of the operating wire. Accordingly, operations of the treatment tool for an endoscope become easy.

It may be arranged such that: the second driving-operation section includes an extending portion which extends towards a rear end side of this treatment tool for an endoscope by way of the first driving-operation section; and the turning member is joined to this extending portion.

It may be arranged such that the second driving-operation section has a shape that is engageable with a thumb, while the first driving-operation section has a shape that is engageable with the other fingers.

Furthermore, it may be arranged such that: a third driving-operation section which forms one unit together with the first driving-operation section is provided on a rear side of the first driving-operation section; a fourth driving-operation section is provided on a rear end of the extending portion; and this fourth driving-operation section is disposed between the first driving-operation section and the third driving-operation section.

In this case, when an operator of the endoscope operates the first driving-operation section and the second driving-operation section, these first driving-operation section and second driving-operation section can be gripped without any difficulties; therefore, the operator of the endoscope can easily operate the treatment tool for an endoscope. On the other hand, when a care assistant standing beside operates the third driving-operation section and the fourth driving-operation section, these third driving-operation section and fourth driving-operation section can be gripped without any difficulties; thereby, enabling easy operation of the treatment tool for an endoscope.

It may be arranged such that the third driving-operation section has a shape that is engageable with a thumb, while the fourth driving-operation section has a shape that is engageable with the other fingers.

It may be arranged such that the first driving-operation section is fixed in a manner such that rotation thereof is restricted with respect to the operating duct section.

In this case, when rotating the first driving-operation section, the operating duct section also rotates together with it. In addition, by rotating the operating duct section, the treatment tool distal end section rotates.

It may be arranged such that the first driving-operation section is provided so as to be rotatable with respect to the operating duct section around an axis of this operating duct section.

In this case, the first driving-operation section can be rotated with respect to the operating duct section. In addition, by rotating the first driving section, the treatment tool distal end section joined thereto rotates with respect to the operating duct section.

It may be arranged such that: the first driving-operation section and the second driving-operation section have shapes which are similar to each other; the third driving-operation section and the fourth driving-operation section have shapes which are similar to each other; and the first driving-operation section and the third driving-operation section have shapes which are different from each other.

In this case, a portion which should be gripped and operated by the operator of the endoscope, and a portion which should be gripped and operated by the care assistant, can be distinguished by the shapes of the first driving-operation section through the fourth driving-operation section.

It may be arranged such that: the first driving-operation section and the second driving-operation section have colors which are the same as each other; the third driving-operation section and the fourth driving-operation section have colors which are the same as each other; and the color of the first driving-operation section is different from the color of the third driving-operation section.

In this case, a portion which should be gripped and operated by the operator of the endoscope, and a portion which should be gripped and operated by the care assistant, can be distinguished by color-coding of the first driving-operation section through the fourth driving-operation section.

It may be provided with a distinguishing means which, at least, combines the first driving-operation section and the second driving-operation section, combines the third driving-operation section and the fourth driving-operation section, and distinguishes the first driving-operation section and the third driving-operation section.

In this case, a portion which should be gripped and operated by the operator of the endoscope, and a portion which should be gripped and operated by the care assistant, can be distinguished by the distinguishing means.

Preferred embodiments of the invention have been explained in the above; however, it should be understood that the present invention is not to be limited to these embodiments. Additions, omissions, substitutions, and other modifications, of the configurations can be made without departing from the spirit or scope of the present invention. The present invention is not to be considered as being limited by the foregoing explanations, and is only limited by the scope of the appended claims.

INDUSTRIAL APPLICABILITY

According to a treatment tool for an endoscope of the present invention, an operating section thereof becomes easy to be gripped and also easy to be operated; thereby, reducing a load on an operator's hand and improving operability thereof.

The invention claimed is:

1. A treatment tool for an endoscope comprising:
an operating duct section which is to be inserted into a forceps channel of the endoscope having a distal end and a proximal end;
a treatment tool which is provided on the distal end of the operating duct section;
an operating wire of which a distal end is joined to the treatment tool and is disposed along the operating duct section;
a turning member of which one end is fixed to a proximal end of the operating wire and is capable of sliding along a longitudinal direction of the operating duct section;
a first driving-operation section which is fixed to the proximal end of the operating duct section with respect to the longitudinal direction and is disposed at a distance from a periphery of the operating duct section in a radial direction; and
a second driving-operation section which is fixed at one end of the turning member and is freely slidable with respect to the first driving-operation section.

2. The treatment tool for an endoscope according to claim 1, wherein the first driving-operation section is used as a second finger-receiving section having a sandwiched section to be sandwiched between the other fingers.

3. The treatment tool for an endoscope according to claim 1, wherein the first finger-receiving section is provided at a position which is on an extension axis line of the operating wire.

4. The treatment tool for an endoscope according to claim 1, wherein the operating duct section is flexible; and
the operating section includes a hard joint-section which connects this operating section onto a forceps opening of the forceps channel so as to make it stand thereon.

5. The treatment tool for an endoscope according to claim 1, wherein a first finger-receiving section is provided at a position which is off an extension axis line of the operating wire.

6. The treatment tool for an endoscope according to claim 5, wherein
the second driving-operation section is a body of which one end is joined to a bottom end of the operating duct section, and stands on the forceps opening while the operating duct section is inserted within the forceps channel; and
the first driving-operation section is a slider section which is joined to a bottom end of the operating wire, and is advanceable and retractable between one end and another end of the body.

7. The treatment tool for an endoscope according to claim 6, wherein the slider section is provided at a position which is on an extension axis line of the operating wire.

8. The treatment tool for an endoscope according to claim 5, wherein
the first finger-receiving section is a thumb hole section through which the thumb is inserted;
the second finger-receiving section is one or a plurality of hole sections through which the other fingers are inserted; and
a linear line connecting between a center of the hole sections and a center of the thumb hole section is in parallel to an advancing-and-retracting direction of a slider section.

9. The treatment tool for an endoscope according to claim 6, wherein a distal end of the body is provided with a hard joint-member which is connected to the forceps channel.

10. The treatment tool for an endoscope according to claim 5, wherein the operating section is provided with an attaching portion which is attached to and is detached from the forceps opening.

11. The treatment tool for an endoscope according to claim 5, further comprising a turning member which folds back the operating wire, and is connected between the first driving-operation section and a bottom end of the operating wire, the turning member having hardness and being formed in substantially a U-shape, wherein
the second driving-operation section is a body of which one end is joined to a bottom end of the operating duct section, and stands on a forceps opening while the operating duct section is inserted within the forceps channel; and
the first driving-operation section is a slider section which is joined to a bottom end of the operating wire, and is advanceable and retractable between one end and another end of the body.

12. The treatment tool for an endoscope according to claim 5, wherein the first driving-operation section is supported beside the operating duct section.

13. The treatment tool for an endoscope according to claim 11, wherein the second driving-operation section is supported beside the operating duct section.

14. The treatment tool for an endoscope according to claim 5, wherein a slider section is provided at a position which is off an extension axis line of the operating wire.

15. The treatment tool for an endoscope according to claim 11, wherein
the first driving-operation section includes an extending portion which extends towards a rear end side of the treatment tool by way of the second driving-operation section; and
the turning member is joined to this extending portion.

16. The treatment tool for an endoscope according to claim 15, wherein a third driving-operation section which forms one unit together with the second driving-operation section is provided on a rear side of the second driving-operation section;
    a fourth driving-operation section is provided on a rear end of the extending portion; and
    the fourth driving operation section is disposed between the second driving-operation section and the third driving-operation section.

17. The treatment tool for an endoscope according to claim 16, wherein the third driving-operation section has a shape engageable with a thumb, while the fourth driving-operation section has a shape engageable with the other fingers.

18. The treatment tool for an endoscope according to claim 16, wherein the second driving-operation section is fixed in a manner such that a rotation thereof is restricted with respect to the operating duct section.

19. The treatment tool for an endoscope according to claim 11, wherein the second driving-operation section is provided so as to be rotatable with respect to the operating duct section around an axis of the operating duct section.

20. The treatment tool for an endoscope according to claim 11, wherein
    the first driving-operation section and the second driving-operation section have shapes which are similar to each other;
    a third driving-operation section and a fourth driving-operation section have shapes which are similar to each other, and
    the first driving-operation section and the third driving-operation section have shapes which are different from each other.

21. The treatment tool for an endoscope according to claim 11, wherein
    the first driving-operation section and the second driving-operation section have colors which are the same as each other;
    a third driving-operation section and a fourth driving-operation section have colors which are the same as each other; and
    color of the first driving driving-operation section is different from color of the third driving-operation section.

22. The treatment tool for an endoscope according to claim 11, further comprising a distinguishing means which, at least, combines the first driving-operation section and the second driving-operation section, combines a third driving-operation section and a fourth driving-operation section, and distinguishes the first driving-operation section and the third driving-operation section.

23. The treatment tool for an endoscope according to claim 1, wherein a bottom end of the operating wire is joined to the first finger-receiving section.

24. The treatment tool for an endoscope according to claim 1, wherein a bottom end of the operating wire is joined to the second finger-receiving section.

25. The treatment tool for an endoscope according to claim 1, wherein the first driving-operation section is connected to the operating duct section so as to rotate around an axis of the operating duct section.

26. The treatment tool for an endoscope according to claim 1, wherein the first driving-operation section is fixed to the operating duct section in the longitudinal direction of the operating duct section.

27. The treatment tool for endoscope according to claim 1, wherein a portion of the turning member is exposed from the operating duct section.

28. The treatment tool for an endoscope according to claim 1, wherein a portion of the turning member is extended in the radial direction from the periphery of the operating duct section.

* * * * *

UNITED STATES PATENT AND TRADEMARK OFFICE
CERTIFICATE OF CORRECTION

| | | |
|---|---|---|
| PATENT NO. | : 7,935,106 B2 | Page 1 of 1 |
| APPLICATION NO. | : 11/366689 | |
| DATED | : May 3, 2011 | |
| INVENTOR(S) | : Tsutomu Okada | |

It is certified that error appears in the above-identified patent and that said Letters Patent is hereby corrected as shown below:

On the Title page, insert item [63]:

--Related U.S. Application Data

(63) Continuation of application No. PCT/JP2004/013293, filed on September 7, 2004.--

Signed and Sealed this
Seventeenth Day of July, 2012

David J. Kappos
*Director of the United States Patent and Trademark Office*